United States Patent
Vanden Hoek et al.

(10) Patent No.: US 6,755,779 B2
(45) Date of Patent: Jun. 29, 2004

(54) APPARATUS AND METHOD FOR DELIVERY OF CARDIAC CONSTRAINT JACKET

(75) Inventors: John C. Vanden Hoek, Elk River, MN (US); Beverly J. Johnson, Arden Hills, MN (US); Jody Rivers, Milaca, MN (US); John David Dockter, Brooklyn Park, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 387 days.

(21) Appl. No.: 09/728,761

(22) Filed: Dec. 1, 2000

(65) Prior Publication Data

US 2002/0068850 A1 Jun. 6, 2002

(51) Int. Cl.[7] .................................................. A61F 2/00
(52) U.S. Cl. .......................... 600/37; 600/16; 600/114; 606/110; 606/111; 606/112; 606/113; 606/114; 606/115; 606/116; 606/127; 606/128; 606/200; 128/898; 604/59
(58) Field of Search ............................. 600/16, 37, 114, 600/562; 606/110, 111, 112, 113, 114, 115, 116, 127, 128, 200; 128/898; 604/59

(56) References Cited

U.S. PATENT DOCUMENTS

| | | | | |
|---|---|---|---|---|
| 5,279,539 A | * | 1/1994 | Bohan et al. | 600/37 |
| 5,337,754 A | * | 8/1994 | Heaven et al. | 128/749 |
| 5,341,815 A | * | 8/1994 | Cofone et al. | 128/749 |
| 5,352,184 A | * | 10/1994 | Goldberg et al. | 600/37 |
| 5,354,303 A | * | 10/1994 | Spaeth et al. | 606/128 |
| 5,366,460 A | * | 11/1994 | Eberbach | 606/151 |
| 5,486,183 A | * | 1/1996 | Middleman et al. | 606/127 |
| 5,647,372 A | * | 7/1997 | Tovey et al. | 128/749 |
| 5,702,343 A | * | 12/1997 | Alferness | 600/37 |
| 5,759,187 A | * | 6/1998 | Nakao et al. | 606/114 |
| 6,077,218 A | * | 6/2000 | Alferness | 600/37 |
| 6,085,754 A | * | 7/2000 | Alferness et al. | 128/898 |
| 6,123,662 A | * | 9/2000 | Alferness et al. | 600/37 |
| 6,126,590 A | * | 10/2000 | Alferness | 600/37 |
| 6,155,972 A | * | 12/2000 | Nauertz et al. | 600/37 |
| 6,165,121 A | * | 12/2000 | Alferness | 600/37 |
| 6,165,122 A | * | 12/2000 | Alferness | 600/37 |
| 6,174,279 B1 | * | 1/2001 | Girard | 600/37 |
| 6,193,648 B1 | * | 2/2001 | Krueger | 600/37 |
| 6,230,714 B1 | * | 5/2001 | Alferness et al. | 128/898 |
| 6,375,608 B1 | * | 4/2002 | Alferness | 600/37 |
| 6,425,856 B1 | * | 7/2002 | Shapland et al. | 600/37 |
| 6,482,146 B1 | * | 11/2002 | Alferness et al. | 600/37 |
| 6,537,203 B1 | * | 3/2003 | Alferness et al. | 600/37 |
| 6,572,533 B1 | * | 6/2003 | Shapland et al. | 600/37 |
| 6,582,355 B2 | * | 6/2003 | Alferness et al. | 600/37 |

FOREIGN PATENT DOCUMENTS

| | | | |
|---|---|---|---|
| DE | 324 524 C | 8/1920 | |
| EP | 0 303 719 A1 | 2/1989 | |
| EP | 0 557 964 A1 * | 9/1993 | ........... A61B/17/00 |
| WO | WO 93 03685 A1 | 3/1993 | |
| WO | WO 00 45735 A1 | 8/2000 | |

* cited by examiner

Primary Examiner—Henry Bennett
Assistant Examiner—Nihir Patel
(74) Attorney, Agent, or Firm—Merchant & Gould P.C.

(57) ABSTRACT

A cardiac constraint jacket is formed of flexible material defining a volume between an open upper end and a lower end. The jacket is dimensioned for an apex of a patient's heart to be inserted into the volume through the open upper end and for the jacket to be slipped over the heart. The jacket includes a receiving member along its upper end for engagement to a delivery apparatus, the apparatus used in positioning the jacket on the heart. The delivery apparatus includes a handle and a band. The band is generally hoop shaped having a first end and a second end attached to the handle, the first end fixedly attached to the handle and the second end releasably attached to the handle. Alternatively, the first end can be attached to a releasable end cap of the handle. In use, the second end of the band is released from the handle and inserted into the jacket receiving member. The jacket is threaded onto the band and the band end re-attached to the handle. The band is deformed to fit over the circumference of the heart, and then manipulated to position the jacket on the heart. Once positioned, the band is released from the handle and removed from the jacket receiving member.

21 Claims, 16 Drawing Sheets

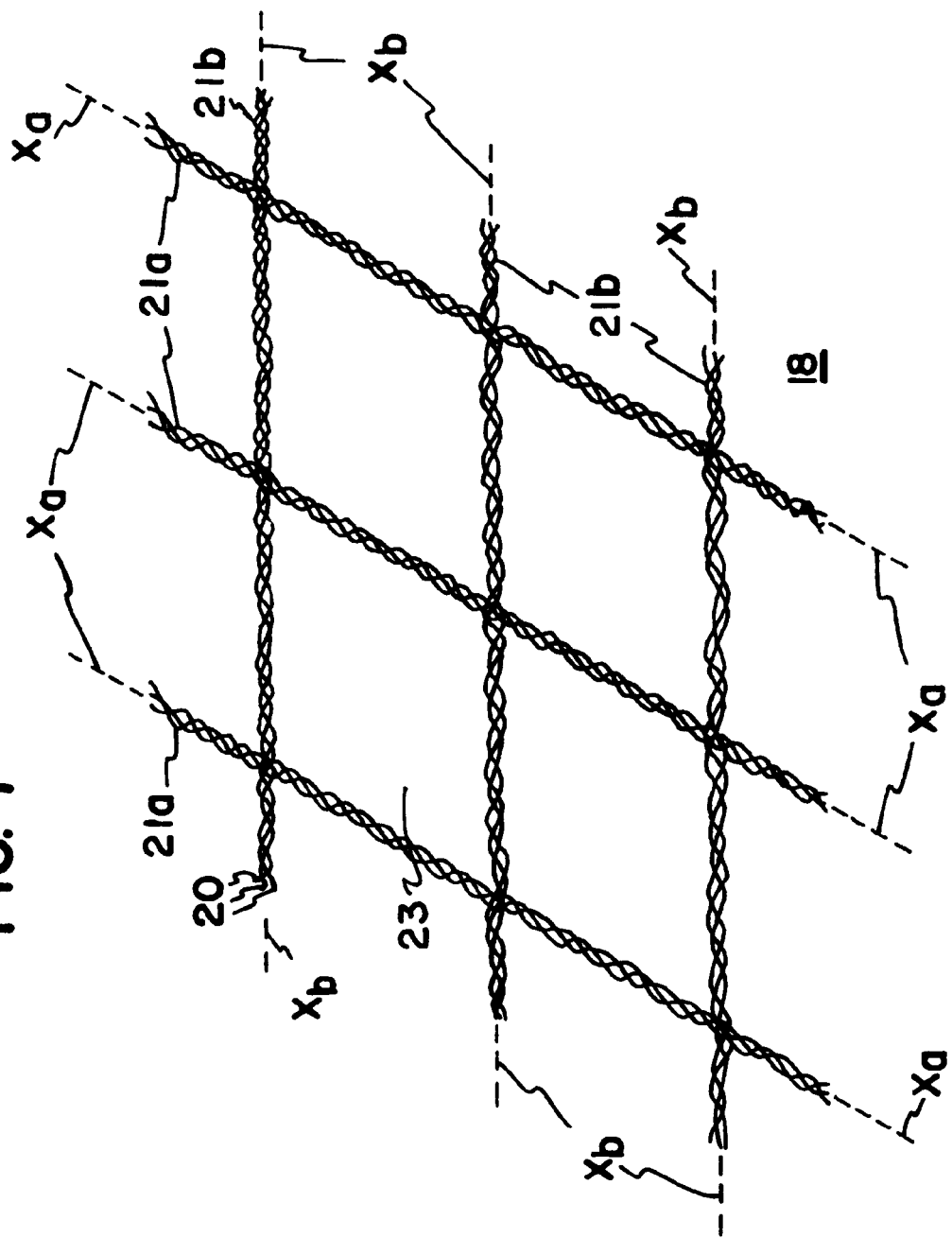

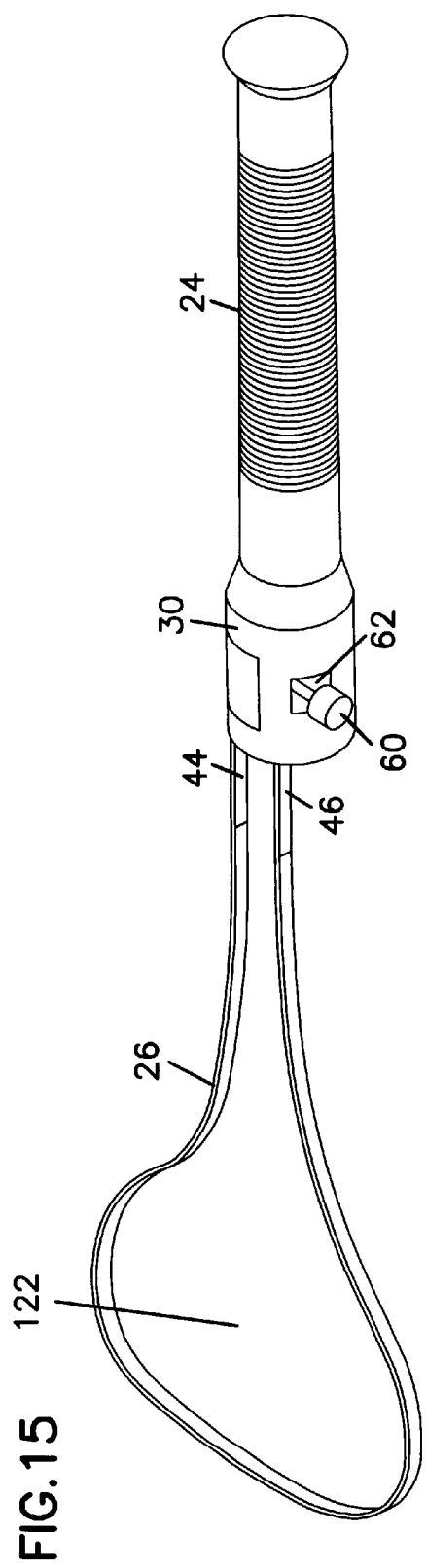

APPARATUS AND METHOD FOR DELIVERY OF CARDIAC CONSTRAINT JACKET

BACKGROUND OF THE INVENTION

1. Field of the Invention

The present invention pertains to a method and apparatus for treating congestive heart disease and related valvular dysfunction. More particularly, the present invention is directed to an apparatus and method for delivery of a cardiac constraint jacket to a heart suffering from the effects of congestive heart disease.

2. Description of the Prior Art

Congestive heart disease is a progressive and debilitating illness. A progressive enlargement of the heart characterizes the disease.

As the heart enlarges, the heart is performing an increasing amount of work in order to pump blood each heartbeat. In time, the heart becomes so enlarged the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Congestive heart failure has an enormous societal impact. In the United States alone, about five million people suffer from the disease (Classes I through IV combined). Alarmingly, congestive heart failure is one of the most rapidly accelerating diseases (about 400,000 new patients in the United States each year). Economic costs of the disease have been estimated at $38 billion annually.

Not surprising, substantial effort has been made to find treatments for congestive heart disease. Recently, a new surgical procedure has been developed. Referred to as the Batista procedure, the surgical technique includes dissecting and removing portions of the heart in order to reduce heart volume. This is a radical new and experimental procedure subject to substantial controversy. Furthermore, the procedure is highly invasive, risky and expensive and commonly includes other expensive procedures (such as a concurrent heart valve replacement).

Clearly, there is a need for alternative treatments applicable to both early and later stages of the disease to either stop the progressive nature of the disease or more drastically slow the progressive nature of congestive heart disease. Unfortunately, currently developed options are experimental, costly and problematic.

Cardiomyoplasty is a recently developed treatment for earlier stage congestive heart disease. In this procedure, the latissimus dorsi muscle (taken from the patient's shoulder) is wrapped around the heart and chronically paced synchronously with ventricular systole. Pacing of the muscle results in muscle contraction to assist the contraction of the heart during systole.

Commonly assigned U.S. Pat. No. 5,702,343 to Alferness dated Dec. 30, 1997 teaches a jacket to constrain cardiac expansion during diastole. Also, PCT International Publication No. WO 98/29401 published Jul. 9, 1998 teaches a cardiac constraint in the form of surfaces on opposite sides of the heart with the surfaces joined together by a cable through the heart or by an external constraint. U.S. Pat. No. 5,800,528 dated Sep. 1, 1998 teaches a passive girdle to surround a heart. German utility model DE 295 17 393 describes a non-expansible heart pouch. PCT International Publication No. WO 98/58598 published Dec. 30, 1998 describes a cardiac pouch with an elastic limit.

A cardiac constraint device can be placed on an enlarged heart and fitted snug during diastole. For example, a knit jacket device can be loosely slipped on the heart. After such placement, the material of the jacket can be gathered to adjust the device to a desired tension. The gathered material can be sutured or otherwise fixed to maintain the tensioning. The heart may be pre-shrunk prior to placement of the device or the device may be fitted on the heart without pre-shrinking the heart. The device is adjusted to a snug fit on the heart during diastole.

The process of placing and fitting the constraint device on the heart often requires a certain amount of direct handling and manipulation of the heart. Excessive manipulation is undesirable since the heart may respond by fibrillating requiring the surgeon to exercise defibrillating procedures or therapies. Additionally, placing the constraint device on the heart is often time consuming and technically difficult.

The present invention is directed to reducing the amount of direct handling of the heart, to reducing the time required to place and fit the constraint jacket on the heart, and to reducing the technical complications required in placing and fitting the jacket on the heart.

SUMMARY OF THE INVENTION

According to a preferred embodiment of the present invention, a method and apparatus are disclosed for treating congestive heart disease and related cardiac complications such as valvular disorders. A cardiac constraint jacket is formed of flexible material defining a volume between an open upper end and a lower end. The jacket is dimensioned for an apex of a patient's heart to be inserted into the volume through the open upper end and for the jacket to be slipped over the heart. A delivery device is used in placing the jacket on the heart.

In one embodiment, the delivery apparatus includes a handle and a band. The band has a first end fastened to the handle and a second end releasably fastened to the handle. The cardiac constraint jacket has a receiving member or other engagement structure to be threaded on the band via the second end of the band for subsequent delivery and positioning of the cardiac constraint jacket on the heart.

In another embodiment, the delivery apparatus includes a handle having a releasable end cap and a band. The band has a first end fastened to the releasable end cap and a second end releasably fastened to the handle. The cardiac constraint jacket has a receiving member or other engagement structure to be threaded on the band via the second end of the band for subsequent delivery and positioning of the cardiac constraint jacket on the heart. The releasable end cap of the handle can be used to limit band recoil during the removal of the band from the cardiac constraint jacket.

The present invention is also a method for constraining a heart undergoing congestive heart disease. The method includes the steps of obtaining a cardiac constraint jacket, obtaining a delivery apparatus having a handle and band, securing the cardiac constraint jacket to the delivery apparatus, positioning the cardiac constraint jacket on the heart using the delivery apparatus and removing the delivery apparatus from the cardiac constraint jacket.

These and various other features as well as advantages which characterize the present invention will be apparent from a reading of the following detailed description and a review of the associated drawings.

BRIEF DESCRIPTION OF THE DRAWINGS

FIG. 7 is an enlarged view of a knit construction of the jacket of the present invention in a rest state;

FIG. 14 is a representative sectional view of the delivery apparatus of FIG. 13;

FIG. 15 is a perspective view illustrating the delivery apparatus having a deformed band;

DESCRIPTION OF THE PREFERRED EMBODIMENT

A. Congestive Heart Disease

Figure 1A:
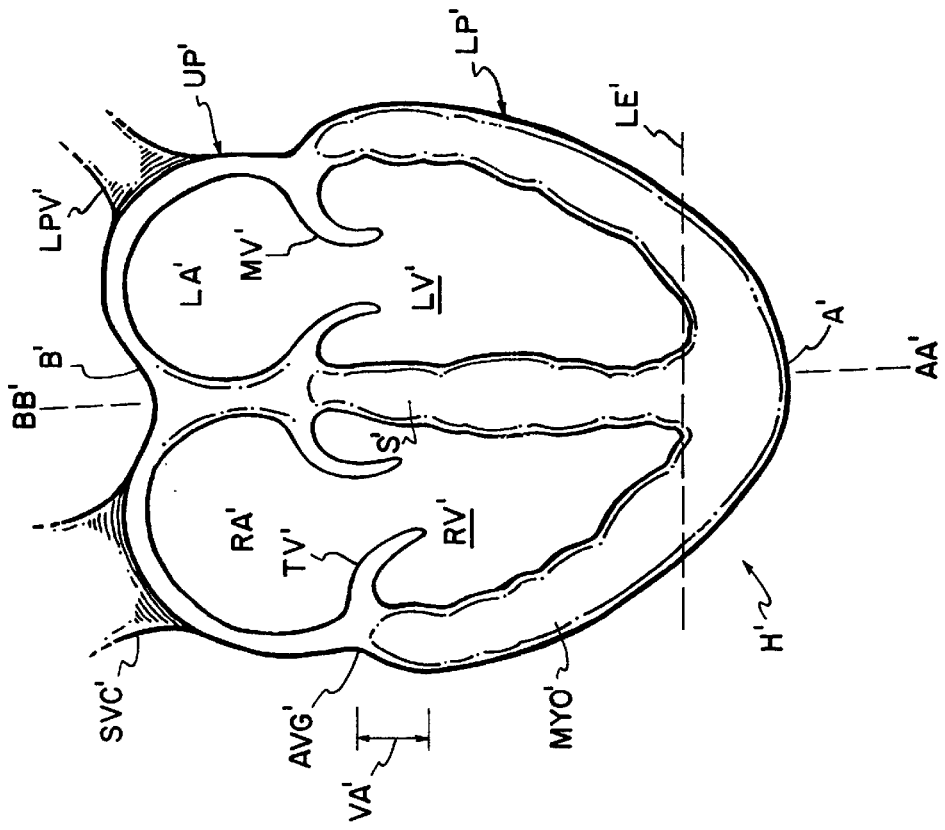
FIG. 1A is the view of FIG. 1 showing the heart during diastole.

To facilitate a better understanding of the present invention, description will first be made of a cardiac constraint device such as is more fully described in commonly assigned U.S. Pat. No. 6,085,754, the disclosure of which is hereby incorporated by reference. In the drawings, similar elements are labeled similarly throughout.

Figure 1:
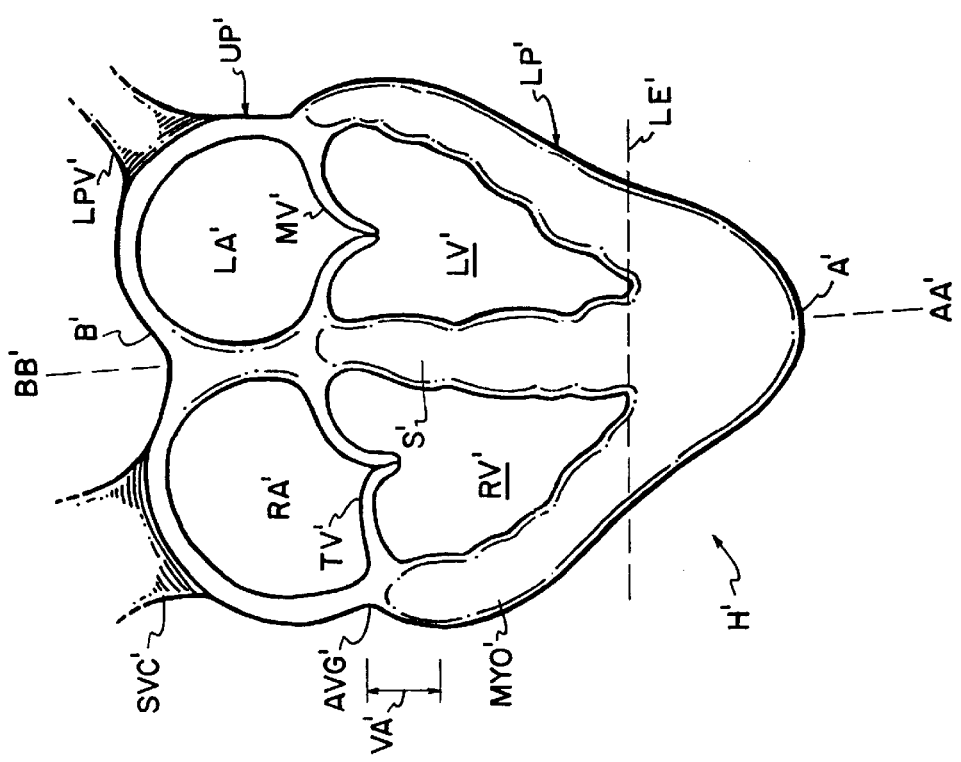
FIG. 1 is a schematic cross-sectional view of a normal, healthy human heart shown during systole.
Figure 1B:
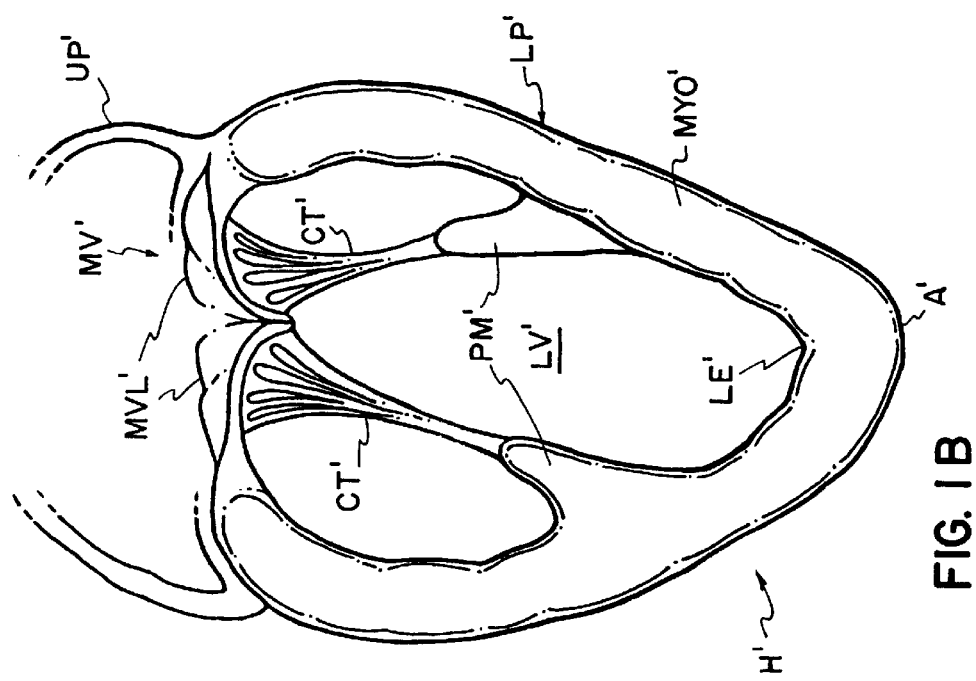
FIG. 1B is a view of a left ventricle of a healthy heart as viewed from a septum and showing a mitral valve.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The myocardium MYO' and septum S' define four internal heart chambers including a right atrium RA', a left atrium LA', a right ventricle RV' and a left ventricle LV'. The heart H' has a length measured along a longitudinal axis BB'–AA' from an upper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A-V (atrio-ventricular) groove AVG'. Extending away from the upper portion UP' are a plurality of major blood vessels communicating with the chambers RA', RV', LA', LV'. For ease of illustration, only the superior vena cava SVC', inferior vena cava IVC' and a left pulmonary vein LPV' are shown as being representative.

The heart H' contains valves to regulate blood flow between the chambers RA', RV', LA', LV' and between the chambers and the major vessels (e.g., the superior vena cava SVC', inferior vena cava IVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A-V groove AVG' and referred to as the valvular annulus VA'. The valves TV' and MV' open and close through the beating cycle of the heart H.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis AA'–BB').

The motion of the heart H' and the variation in the shape of the heart H' during contraction and expansion is complex. The amount of motion varies considerably throughout the heart H'. The motion includes a component which is parallel to the axis AA'–BB' (conveniently referred to as longitudinal expansion or contraction). The motion also includes a component perpendicular to the axis AA'–BB' (conveniently referred to as circumferential expansion or contraction).

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Figure 2B:
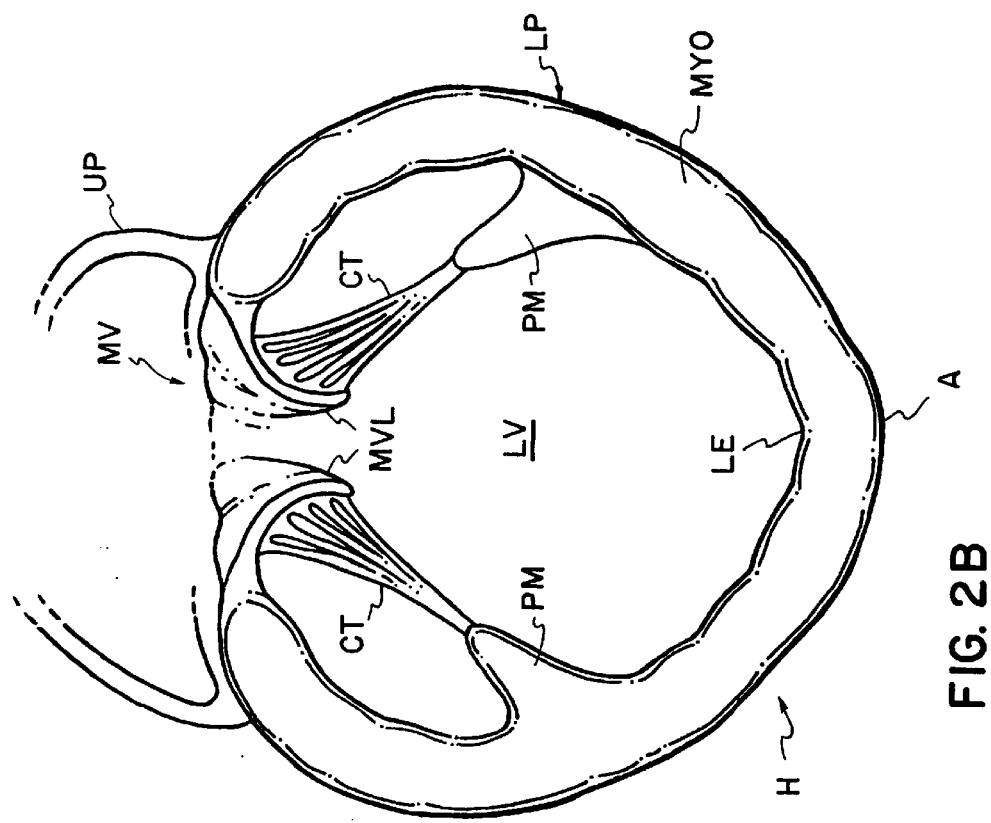
FIG. 2B is the view of FIG. 1B showing a diseased heart.
Figure 2A:
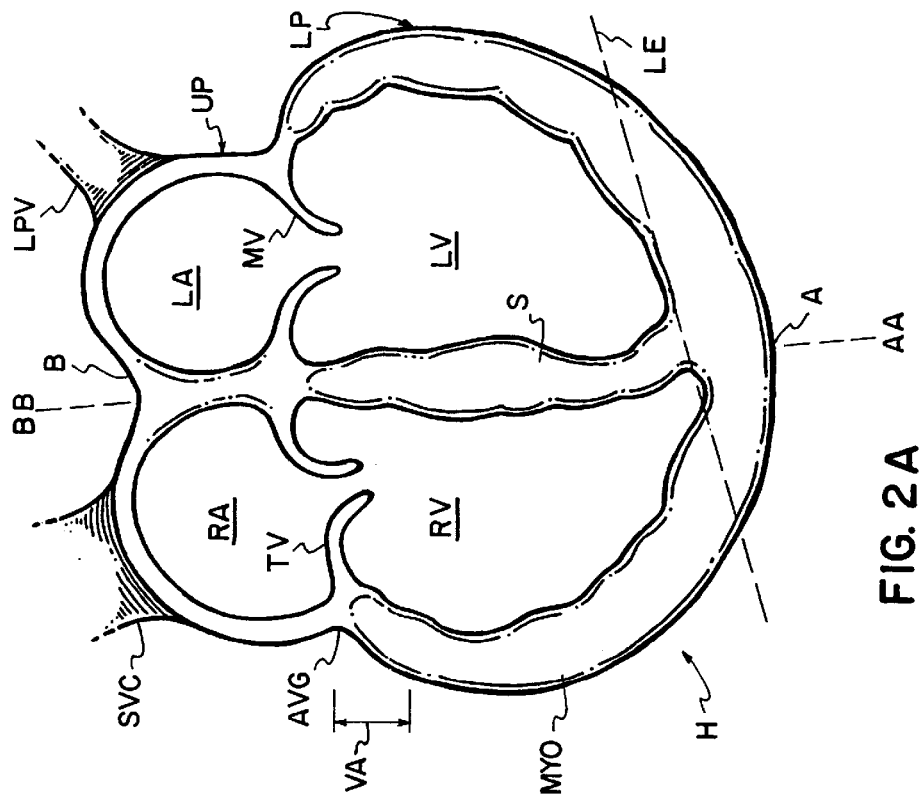
FIG. 2A is the view of FIG. 2 showing the heart during diastole.
Figure 2:
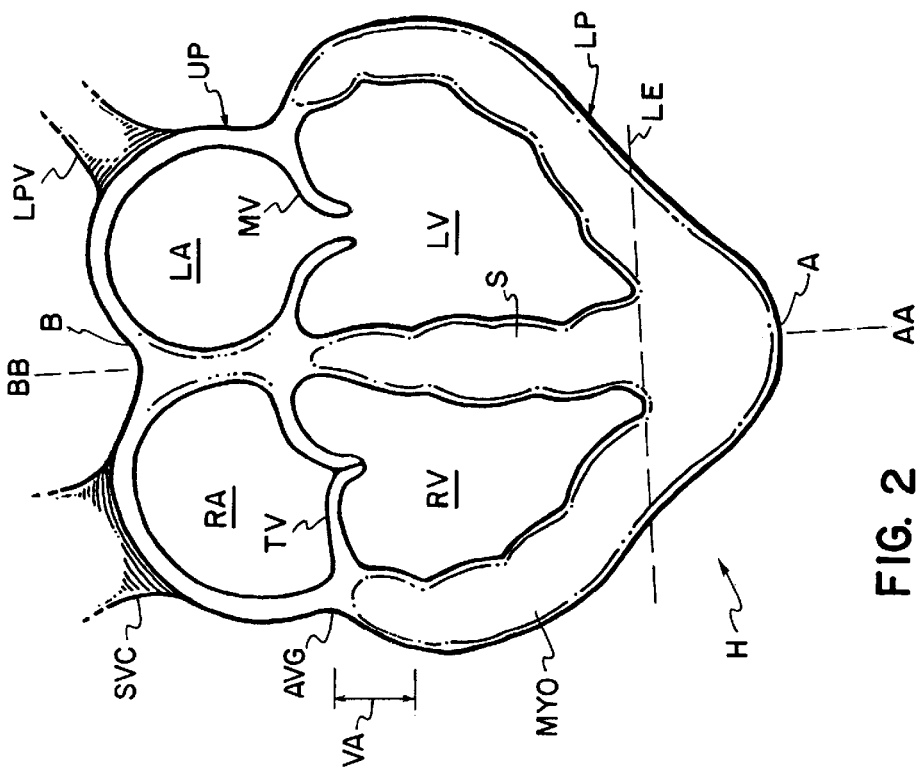
FIG. 2 is a schematic cross-sectional view of a diseased human heart shown during systole.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H dilates outwardly between the apex A and the A-V groove AVG. So deformed, the diseased heart H during systole (FIG. 2) resembles the healthy heart H' during diastole (FIG. 1A). During diastole (FIG. 2A), the deformation is even more extreme.

As a diseased heart H enlarges from the representation of FIGS. 1 and 1A to that of FIGS. 2 and 2A, the heart H becomes a progressively inefficient pump. Therefore, the heart H requires more energy to pump the same amount of blood. Continued progression of the disease results in the heart H being unable to supply adequate blood to the patient's body and the patient becomes symptomatic of cardiac insufficiency.

For ease of illustration, the progression of congestive heart disease has been illustrated and described with reference to a progressive dilation of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close. Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H.

B. Cardiac Constraint Therapy

Having described the characteristics and problems of congestive heart disease, a treatment method and apparatus are described in commonly assigned U.S. Pat. No. 6,085,754. In general, a jacket is configured to surround the myocardium MYO. While the method of the present invention will be described with reference to a jacket as described in U.S. Pat. No. 6,085,754, it will be appreciated the present invention is applicable to any cardiac constraint device including those shown in U.S. Pat. No. 5,800,528 and PCT International Publication No. WO 98/29401. The entire disclosure of each of these documents is incorporated herein by reference.

Figure 3A:
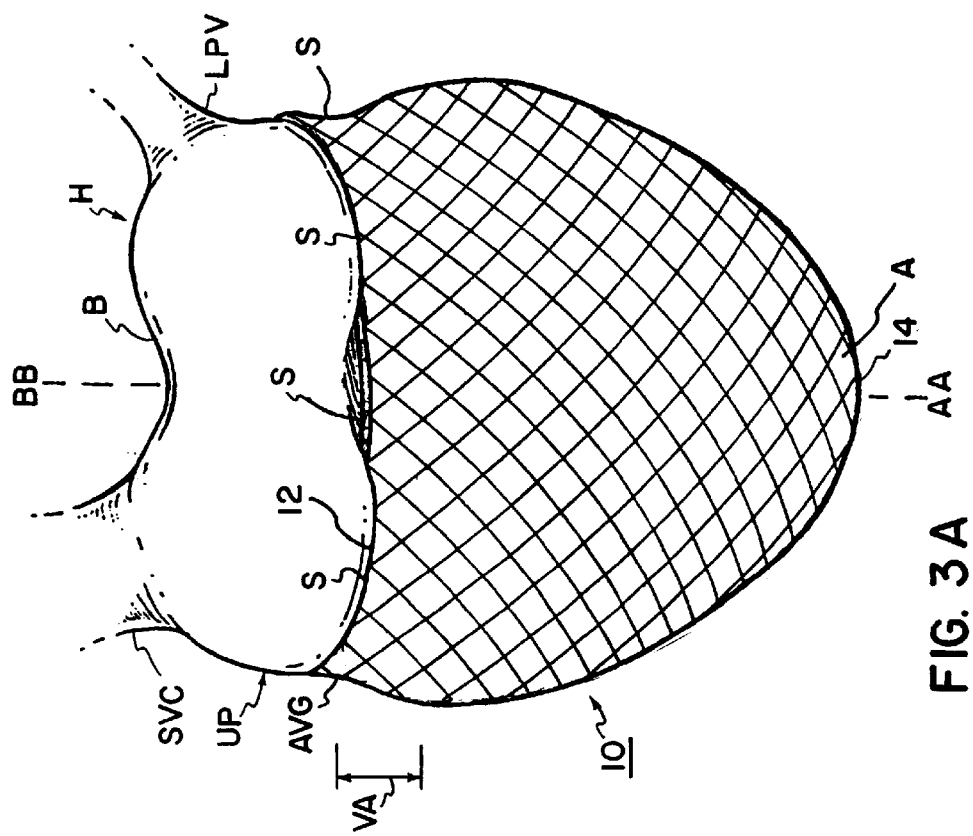
FIG. 3A is a side elevation view of a diseased heart in diastole with the jacket of FIG. 3 in place.
Figure 3:
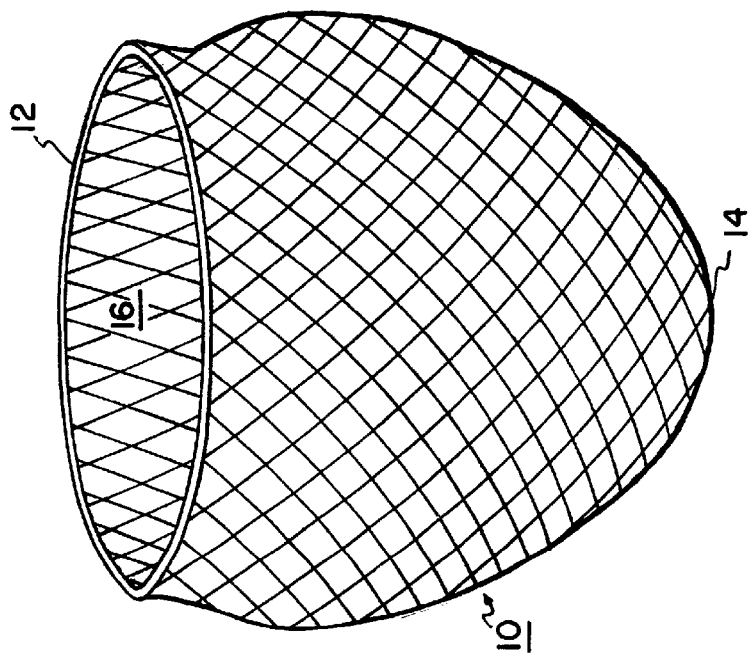
FIG. 3 is a perspective view of a cardiac constraint jacket.
Figure 4A:
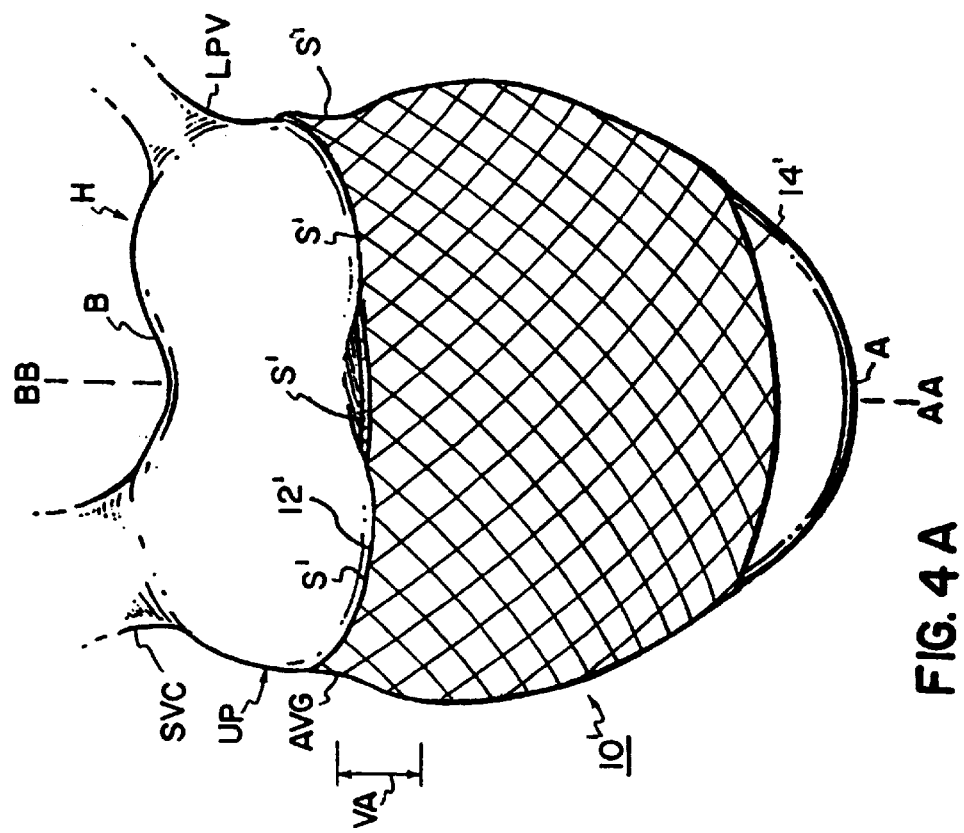
FIG. 4A is a side elevation view of a diseased heart in diastole with the jacket of FIG. 4 in place.
Figure 4:
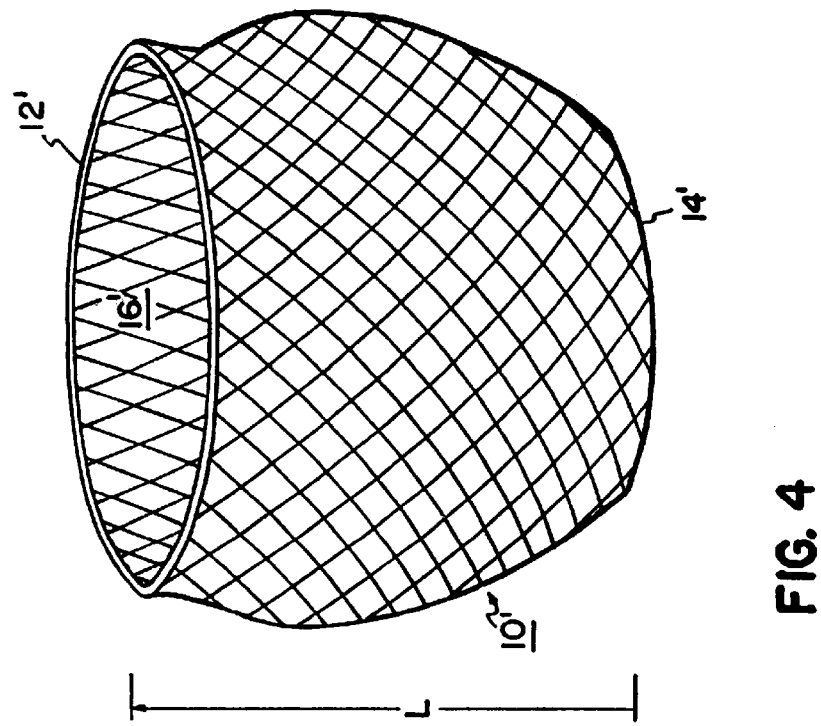
FIG. 4 is a perspective view of an alternative cardiac constraint jacket.

With reference now to FIGS. 3, 3A, 4 and 4A, the cardiac constraint device is shown as a jacket 10, 10' of flexible, biologically compatible material. The jacket 10, 10' is an enclosed knit material having upper and lower ends 12, 12', 14, 14'. The jacket 10, 10' defines an internal volume 16, 16' which is completely enclosed but for the open ends 12, 12' and 14'. In the embodiment of FIG. 3, lower end 14 is closed. In the embodiment of FIG. 4, lower end 14' is open. In both embodiments, upper ends 12, 12' are open. Throughout this description, the embodiment of FIG. 3 will be discussed. Elements in common between the embodiments of FIGS. 3 and 4 are numbered identically with the addition of an apostrophe to distinguish the second embodiment and such elements need not be separately discussed.

Figure 5:
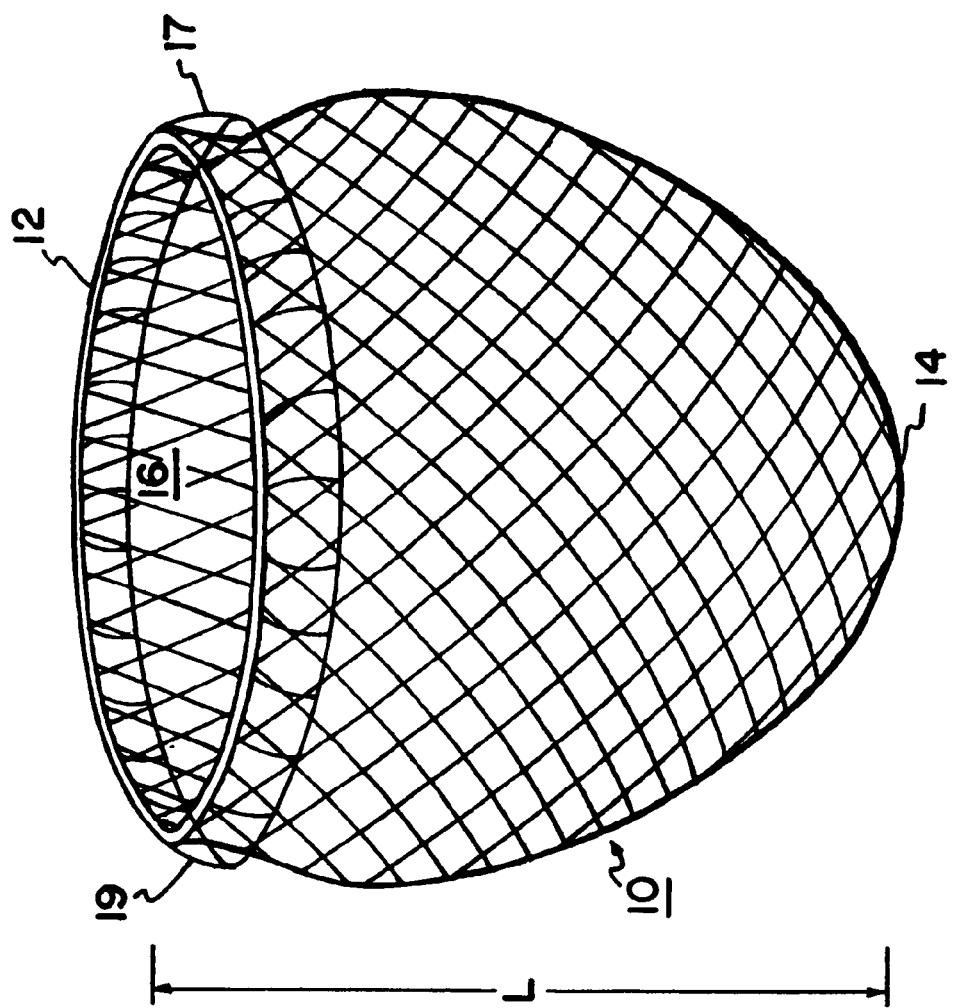
FIG. 5 is a cross-sectional view of the jacket illustrating a receiving member for use in delivery of the jacket on the heart.

The jacket 10 is dimensioned with respect to a heart H to be treated. Specifically, the jacket 10 is sized for the heart H to be constrained within the volume 16. Some embodiments of the jacket 10 include a receiving member 17 around the upper end 12 for receiving the delivery apparatus of the present invention, as shown in FIG. 5. The receiving member may be continuous or discontinuous, but there must be at least two points along the upper end of the jacket for receiving the delivery apparatus of the present invention. Receiving members for use in the present invention include, but are not limited to, a seam, a sleeve, a series of loops, etc. As discussed in greater detail below, the delivery apparatus is used to facilitate placement of the jacket 10 around the heart H. Although not shown, a receiving member 17 may also be positioned around the upper end 12 of the jacket 10 having an open lower end 14' (see FIG. 4). Note also that exact placement of the receiving member around the upper end of the jacket is not critical to the placement of the jacket on the heart. Rather, the receiving member must be positioned on the jacket so as to receive the delivery apparatus and function to hold the jacket open for accurate placement around the heart.

The jacket 10 has a length L between the upper and lower ends 12, 14 sufficient for the jacket 10 to constrain the lower portion LP. The upper end 12 of the jacket 10 preferably extends at least to A-V groove AVG and further extends to the lower portion LP to constrain at least the lower ventricular extremities LE.

When the parietal pericardium is opened, the lower portion LP is free of obstructions for applying the jacket 10 over the apex A. If, however, the parietal pericardium is intact, the diaphragmatic attachment to the parietal pericardium inhibits application of the jacket over the apex A of the heart. In this situation, the jacket can be opened along a line extending from the upper end 12' to the lower end 14' of jacket 10'. As discussed in greater detail below, an embodiment of the delivery apparatus of the present invention may be used to place the opened jacket 10 around the pericardial surface of the heart H. Once placed, the opposing edges of the jacket's opened line are secured together. Systems for securing the opposing edges are disclosed in, for example, U.S. Pat. No. 5,702,343, the entire disclosure of which is incorporated herein by reference. The lower end 14' can then be secured to the diaphragm or associated tissues using, for example, sutures, staples, etc.

In the embodiment of FIGS. 3 and 3A, the lower end 14 is closed and the length L is sized for the apex A of the heart H to be received within the lower end 14 when the upper end 12 is placed at the A-V groove AVG. In the embodiment of FIGS. 4 and 4A, the lower end 14' is open and the length L' is sized for the apex A of the heart H to protrude beyond the lower end 14' when the upper end 12' is placed at the A-V groove AVG. The length L' is sized so that the lower end 14' extends beyond the lower ventricular extremities LE such that in both of jackets 10, 10', the myocardium MYO surrounding the ventricles RV, LV is in direct opposition to material of the jacket 10, 10' during diastole. Such placement is desirable for the jacket 10, 10' to present a constraint against dilation of the ventricular portions of the heart H.

After the jacket 10 is positioned on the heart H as described above, the jacket 10 is secured to the heart. Preferably, the jacket 10 is secured to the heart H using sutures (or other fastening means such as staples). The jacket 10 is sutured to the heart H at suture locations S circumferentially spaced along the upper end 12. While a surgeon may elect to add additional suture locations to prevent shifting of the jacket 10 after placement, the number of such locations S is preferably limited so that the jacket 10 does not restrict contraction of the heart H during systole.

The jacket 10 constrains further undesirable circumferential enlargement of the heart while not impeding other motion of the heart H. With the benefits of the present teachings, numerous modifications are possible. For example, the jacket 10 need not be directly applied to the epicardium (i.e., outer surface of the myocardium) but could be placed over the parietal pericardium. Further, an anti-fibrosis lining (such as a PTFE coating on the fibers of the knit) could be placed between the heart H and the jacket 10. Alternatively, the fibers 20 can be coated with PTFE.

The jacket 10 can be used in early stages of congestive heart disease. For patients facing heart enlargement due to viral infection, the jacket 10 permits constraint of the heart H for a sufficient time to permit the viral infection to pass. In addition to preventing further heart enlargement, the jacket 10 treats valvular disorders by constraining circumferential enlargement of the valvular annulus and deformation of the ventricular walls.

C. Tensioning of the Jacket

Figure 6:
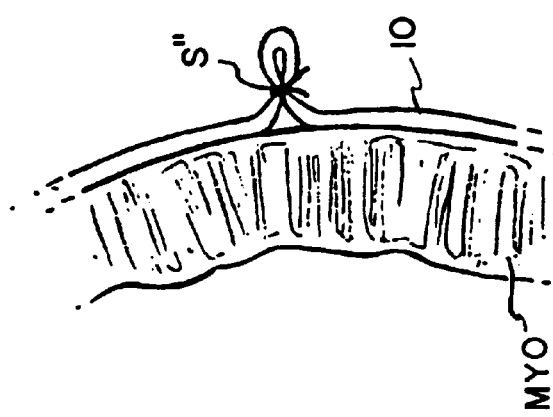
FIG. 6 is a cross-sectional view of the jacket of FIG. 3 overlying a myocardium and with the material of the device gathered for a snug fit.

To permit the jacket 10 to be easily placed on the heart H, the volume and shape of the jacket 10 are larger than the lower portion LP during diastole. So sized, the jacket 10 may be easily slipped around the heart H using the delivery apparatus of the present invention (see below). Once placed, the jacket's volume and shape are adjusted for the jacket 10 to snugly conform to the external geometry of the heart H during diastole. Such sizing is easily accomplished due to the knit construction of the jacket 10. For example, excess material of the jacket 10 can be gathered and sutured S" (FIG. 6) to reduce the volume 16 of the jacket 10 and conform the jacket 10 to the shape of the heart H during diastole. Such shape represents a maximum adjusted volume. The jacket 10 constrains enlargement of the heart H beyond the maximum adjusted volume while preventing restricted contraction of the heart H during systole. As an alternative to gathering of FIG. 6, the jacket 10 can be provided with other arrangements for adjusting and determining the volume of the jacket. For example, as disclosed in U.S. Pat. No. 5,702,343, the jacket can be provided with a slot. The jacket can alternatively include, for example, tension indicators as disclosed in co-pending U.S. Ser. No. 09/400,018 or tensioning arrangements as disclosed in co-pending U.S. Ser. No. 09/400,019. The entire disclosure of each of these applications is hereby incorporated herein by reference.

The jacket 10 is adjusted to a snug fit on the heart H during diastole. Care is taken to avoid tightening the jacket 10 too much such that cardiac function is impaired. During diastole, the left ventricle LV fills with blood. If the jacket 10 is too tight, the left ventricle LV cannot adequately expand and left ventricular pressure will rise. During the fitting of the jacket 10, the surgeon can monitor left ventricular pressure. For example, a well-known technique for monitoring so-called pulmonary wedge pressure uses a catheter placed in the pulmonary artery. The wedge pressure provides an indication of filling pressure in the left atrium LA and left ventricle LV. While minor increases in pressure (e.g., 2–3 mm Hg) can be tolerated, the jacket 10 is snugly fit on the heart H but not so tight as to cause a significant increase in left ventricular pressure during diastole.

As mentioned, the jacket 10 is constructed from a knit, biocompatible material. The knit 18 is illustrated in FIG. 7. Preferably, the knit is a so-called "Atlas knit" well known in the fabric industry. The Atlas knit is described in Paling, *Warp Knitting Technology*, p. 111, Columbine Press (Publishers) Ltd., Buxton, Great Britain (1970).

The Atlas knit is a knit of fibers 20 having directional expansion properties. More specifically, the knit 18, although formed of generally inelastic fibers 20, permits a construction of a flexible fabric at least slightly expandable beyond a rest state. FIG. 7 illustrates the knit 18 in a rest state. The fibers 20 of the fabric 18 are woven into two sets of fiber strands 21a, 21b having longitudinal axes $X_a$ and $X_b$. The strands 21a, 21b are interwoven to form the fabric 18 with strands 21a generally parallel and spaced-apart and with strands 21b generally parallel and spaced-apart. It is also envisioned that preferable embodiments of the receiving member 17 are constructed from fibers 20 of fabric 18. For example, one possible receiving member using fibers 20 is a series of individual spaced apart loops 19 along the upper end of the jacket.

Figure 8:
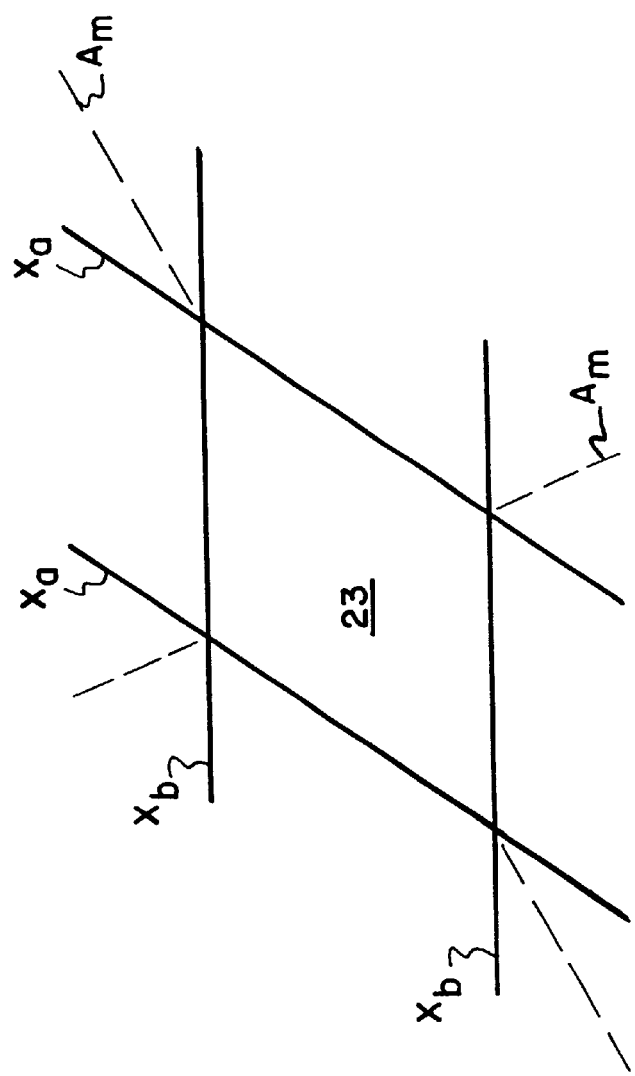
FIG. 8 is a schematic view of the material of FIG. 7.

For ease of illustration, fabric 18 is schematically shown in FIG. 8 with the axis of the strands 21a, 21b only being shown. The strands 21a, 21b are interwoven with the axes $X_a$ and $X_b$ defining a diamond-shaped open cell 23 having diagonal axes $A_m$. In a preferred embodiment, the axes $A_m$ are 5 mm in length when the fabric 18 is at rest and not stretched. The fabric 18 can stretch in response to a force. For any given force, the fabric 18 stretches most when the force is applied parallel to the diagonal axes $A_m$. The fabric 18 stretches least when the force is applied parallel to the strand axes $X_a$ and $X_b$. The jacket 10 is constructed for the material of the knit to be directionally aligned for a diagonal axis $A_m$ to be parallel to the heart's longitudinal axis AA–BB.

While the jacket 10 is expandable due to the above-described knit pattern, the fibers 20 of the knit 18 are preferably non-expandable. While all materials expand to at least a small amount, the fibers 20 are preferably formed of a material with a low modulus of elasticity. In response to the low pressures in the heart H during diastole, the fibers 20 are non-elastic. In a preferred embodiment, the fibers are 70 Denier polyester. While polyester is presently preferred, other suitable materials include polytetrafluoroethylene (PTFE), expanded PTFE (ePTFE), polypropylene and stainless steel.

The knit material has numerous advantages. Such a material is flexible to permit unrestricted movement of the heart H (other than the desired constraint on circumferential expansion). The material is open defining a plurality of interstitial spaces for fluid penneability as well as minimizing the amount of surface area of direct contact between the heart H and the material of the jacket 10 (thereby minimizing areas of irritation or abrasion) to minimize fibrosis and scar tissue.

The open areas of the knit construction also allows for electrical connection between the heart and surrounding tissue for passage of electrical current to and from the heart. For example, although the knit material is an electrical insulator, the open knit construction is sufficiently electrically permeable to permit the use of trans-chest defibrillation of the heart. Also, the open, flexible construction permits passage of electrical elements (e.g., pacer leads) through the jacket. Additionally, the open construction permits other procedures, e.g., coronary bypass, to be performed without removal of the jacket.

A large open area for cells 23 is desirable to minimize the amount of surface area of the heart H in contact with the material of the jacket 10 (thereby reducing fibrosis). However, if the cell area 23 is too large, localized aneurysm can form. Also, a strand 21a, 21b can overly a coronary vessel with sufficient force to partially block the vessel. A smaller cell size increases the number of strands thereby decreasing the restricting force per strand. Preferably, a maximum cell area is no greater than about 6.45 cm$^2$ (about 2.54 cm by 2.54 cm) and, more preferably, is about 0.25 cm$^2$ (about 0.5 cm by 0.5 cm). The maximum cell area is the area of a cell 23 after the material of the jacket 10 is fully stretched and adjusted to the maximum adjusted volume on the heart H as previously described.

The fabric 18 is preferably tear and run resistant. In the event of a material defect or inadvertent tear, such a defect or tear is restricted from propagation by reason of the knit construction.

D. The Delivery Apparatus

Figure 9:
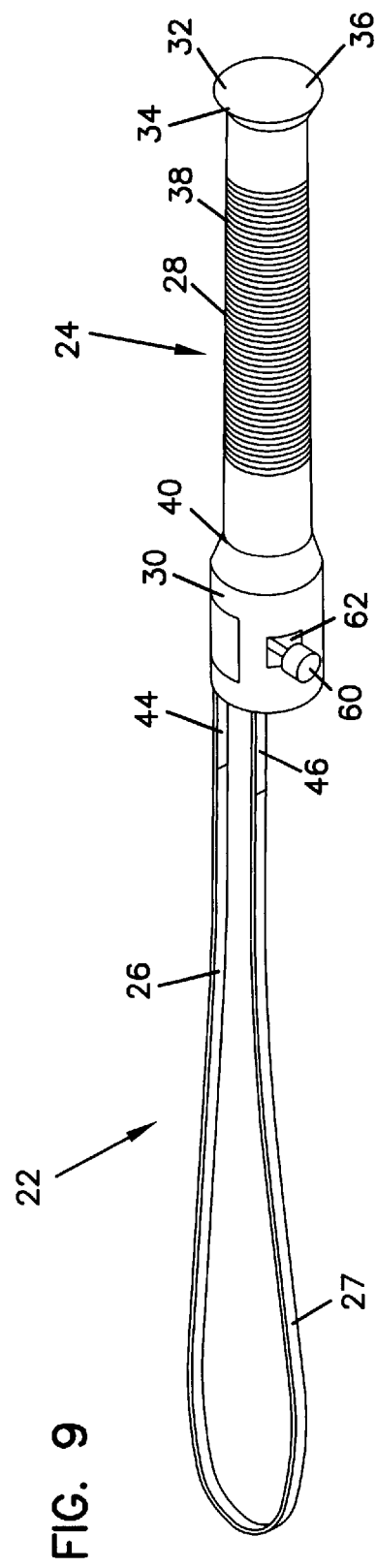
FIG. 9 is a perspective view of one embodiment of the delivery apparatus of the present invention in a closed position.

One embodiment of the delivery apparatus is shown in FIG. 9. The delivery apparatus 22 of the present invention facilitates delivery or application of a jacket 10 to the heart H. The delivery apparatus 22, includes a handle 24 for gripping the apparatus and a flat hoop shaped band 26 for engagement with, and manipulation of, the cardiac constraint jacket 10.

The handle 24 is made of a rigid material, such as plastic, metal or other material with suitable structural properties. Handle 24 materials are preferably non-reactive with alcohol or other sterilizing agents. Further, preferable handle 24 materials are able to withstand temperatures and pressures associated with standard hospital autoclaving techniques. One such material is Ultem (polyetherimide), manufactured by Monsanto.

The handle 24 of the delivery apparatus 22 has a substantially cylindrical shape, although other shapes are contemplated to be within the scope of the present invention. The handle 24 includes a grip portion 28 and an engagement portion 30. In one embodiment, the grip portion 28 has a narrower diameter than the engagement portion 30, optimized for fitting the average adult grip. In a preferred embodiment, a lateral extension 34 extends from the first end 32 of the grip portion 28 to support and add leverage to a user's hand during use of the device. The lateral extension of the grip portion 28 preferably has a flat bottom 36 that may be used to rest the delivery device in an upright position.

The grip portion surface may be smooth or covered with friction enhancing material 38, such as silicone or rubber. Friction enhancing material 38, like the material used to make the handle, is preferably able to withstand typical autoclave temperatures and pressures used in the sterilization of surgical equipment. The grip portion 28 may also be textured or define form fitted indentations (not shown) to enhance and optimize the frictional engagement between the user's hand and the grip portion of the handle.

Figure 11:
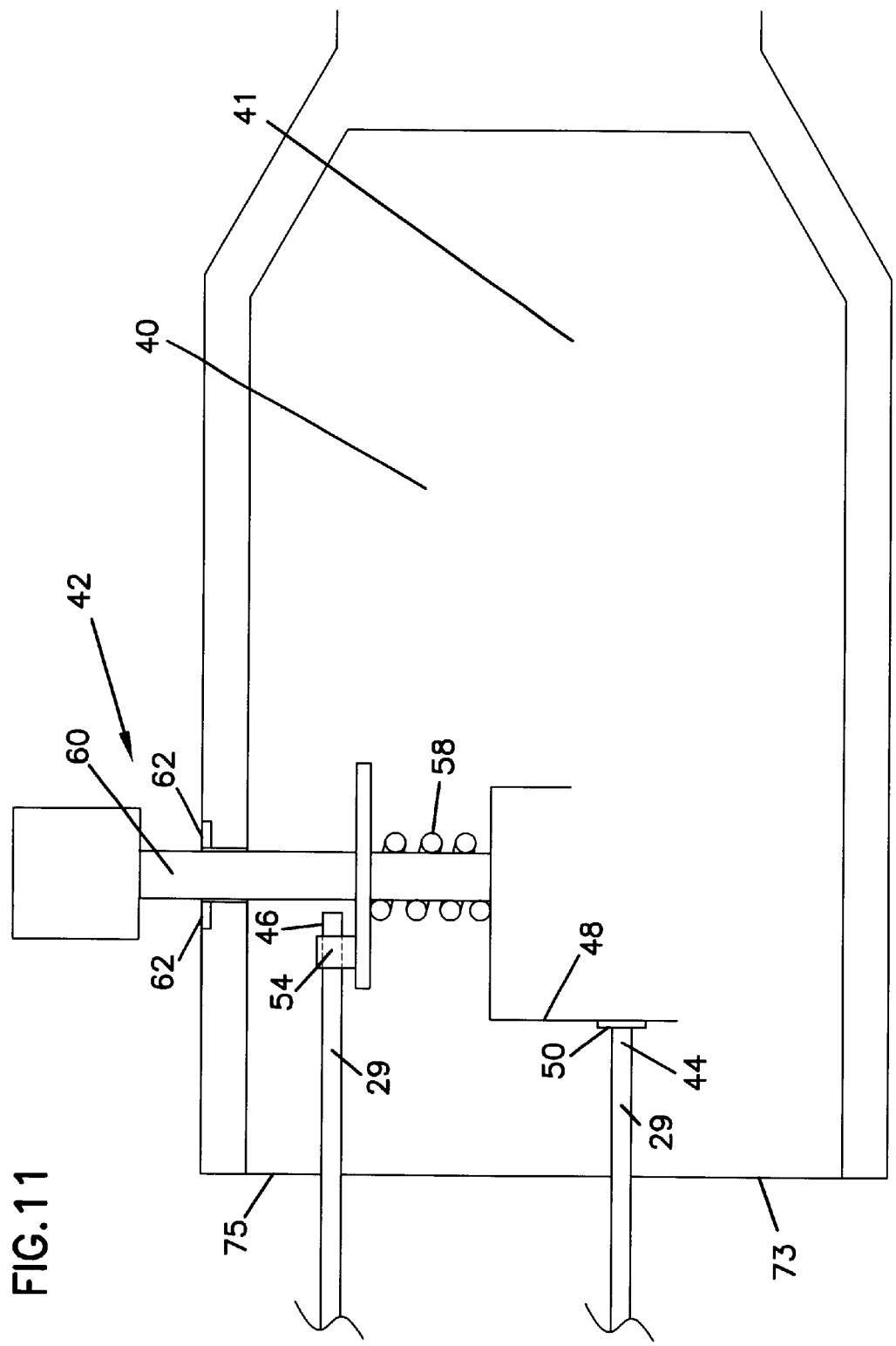
FIG. 11 is a representative cross sectional view illustrating one embodiment of the releasing mechanism of the delivery apparatus of FIG. 9.

The engagement portion 30 of the handle 24 is functionally contiguous with the grip portion 28, and as noted above, may have a slightly larger diameter than the grip portion. Preferably, the interior 40 of at least the engagement portion 30 defines a cavity 41 for housing the releasing mechanism 42 for the band 26, as is discussed in greater detail below. A second end of the handle 73 (i.e., opposite the first end of the grip portion) located on the engagement portion has a face 75 for protecting the interior 40 of the engagement portion of the handle. Generally, two slots 43 and 45 are formed in the face for receiving a first end 44 and a second end 46 of the band 26 respectively (see FIG. 11). In an alternative embodiment, the end of the engagement portion may be open, allowing an unobstructed opening to the interior cavity 41 of the engagement portion 30.

The hoop shaped band 26 of the present invention is typically constructed of a flexible yet, sturdy material, for example plastic or metal. Generally, the band has an exposed portion 27, i.e., exposed to the outside of the handle, and a contained portion 29, i.e., contained within the handle. Typically, the exposed band 27 is sufficient in length to encompass the circumference of the heart H. Typical lengths of the exposed portion 27 of the band 26 are from 300 to 600 millimeters (mm), preferably from 390 to 550 mm, and most preferably from 430 to 550 mm. Additionally, the delivery apparatus 22 may be manufactured and sold having different lengths of exposed bands. For example, an operating room may have a set of delivery apparatus 22, where a set would have a series of standardized length of exposed bands 27, for example, devices having short (432–472 mm), medium (475–515 mm), and long (520–560 mm) lengths for use with small, medium and large hearts respectively.

In a preferred embodiment of the present invention, the band 26 exhibits a "flat" or low profile, having a band thickness of 0.4 mm to 0.9 mm, and a preferred thickness of approximately about 0.6 mm to about 0.8 mm, and a width of approximately 2 to 4 mm, and a preferred width of about 3 mm to about 4 mm. The flat or low profile of the band allows the band, when shaped into a hoop, to be manipulated and compressed into small spaces like a surgical cavity or through small incisions. In contrast, the wider width of the band provides a measure of rigidity in the lateral direction which allows the hoop shaped band to move up and around the heart while maintaining the hoop's pre-existing shape, especially when positioning the cardiac constraint jacket on the heart, as is discussed in greater detail below. Note, however, that other embodiments of the present invention have band cross sectional shapes that may include, but are not limited to, round, oval, triangular, etc. Note also that the edges of the flat or low profile shaped band are preferably rounded to remove any sharp edges from the band. Additionally, the second end of the band is preferably tapered in the width and thickness directions for facilitating the smooth entry of the band tip onto the receiving member of the cardiac constraint jacket.

Composite materials and metal are the preferable materials for construction of the hoop shaped band 26. Typical composite materials include, but are not limited to, elongated carbon, Kevlar™ fibers and epoxy, etc. Typical metals for use in the band 26 include, but are not limited to, nickel-titanium alloys, e.g., nitinol, titanium alloys, stainless steel, and aluminum. The most preferable band material is prepared from a shape memory activated alloy, most preferably nitinol. Shape memory alloys, due to inherent phase transformation characteristics of the alloy, exhibit shape memory, superelasticity, resistance to permanent deformation, and durability, all of which are useful in the present invention.

As discussed above, the band is preferably made from nitinol and is heat set into a hoop like shape that mimics the shape of the cardiac constraint jacket hem that fits the jacket to the heart. The superelastic properties of the heat set nitinol allow the hoop to be "flattened" or elongated into a compressed hoop that fits through narrow incisions in the patient, after which it can be re-expanded in the patient's chest cavity to the hoop's original shape for fitting around the heart (see FIGS. 11 and 15).

In another embodiment of the present invention, the nitinol band is heat treated to create variable zones of stiffness along the exposed length of the band. Each zone can be manipulated through heat treatment to have a differing degree of superelasticity, elasticity and malleability. The combination and placement of these zones along the band is used to improve the user's ability to manipulate and shape the band. A properly treated band has a pre-set hoop like shape that can be "flattened" for manipulation and re-shaped into a hoop for placement of the jacket around the heart.

In another embodiment of the present invention, a substantial length of the band has a first malleability, and the remainder of the band has a second malleability, where the second malleability is greater or more malleable than the first malleability. Preferably, the second malleability is located at the second end of the band, typically the final 10 to 30 mm of the band, and preferably the final 15 to 25 mm of the band. The region of the band having the second malleable state is able to conform to the anatomical shape of whatever that region of the band is being pulled across. As such, as the band is withdrawn from the heart, the second end provides little resistance, i.e., it will distort, to the structures of the heart or cardiac constraint jacket and thus minimizes the possibility that the end of the band will disrupt or damage these structures.

In another embodiment of the present invention, the second malleable state of the band is a separate malleable piece form fitted onto the band just prior to use.

In addition, an embodiment of the present invention is a metal band that has been annealed or tempered over its entire length so as to reduce stress and brittleness in the metal. Reduced metal stress and brittleness helps to maximize the life span of the band. Typical heating and cooling cycles required to anneal the band are well known in the art.

The invention has several different releasing mechanism embodiments for releasing at least one end of the band from the handle. One embodiment of the releasing mechanism has the first end 44 of the band mounted to the engagement portion 30 of the handle 24, preferably at the interior surface 48 of the engagement portion. Attachment is through any number of well known means, including, but not limited to, adhesives, brackets, bolts, rivets, screws, mating slots, insert molding, contained enlarged or bent end, pin through a hole, etc. From the attachment site 50 of the first end 44 of the band 26, the band 26 extends away from the engagement portion to form a substantially hoop like structure that releasably attaches at its second end 46 to a releasing mechanism 42 on the device. Preferably, the releasing mechanism is located at the engagement portion 30, more preferably at the interior of the engagement portion.

Figure 10:
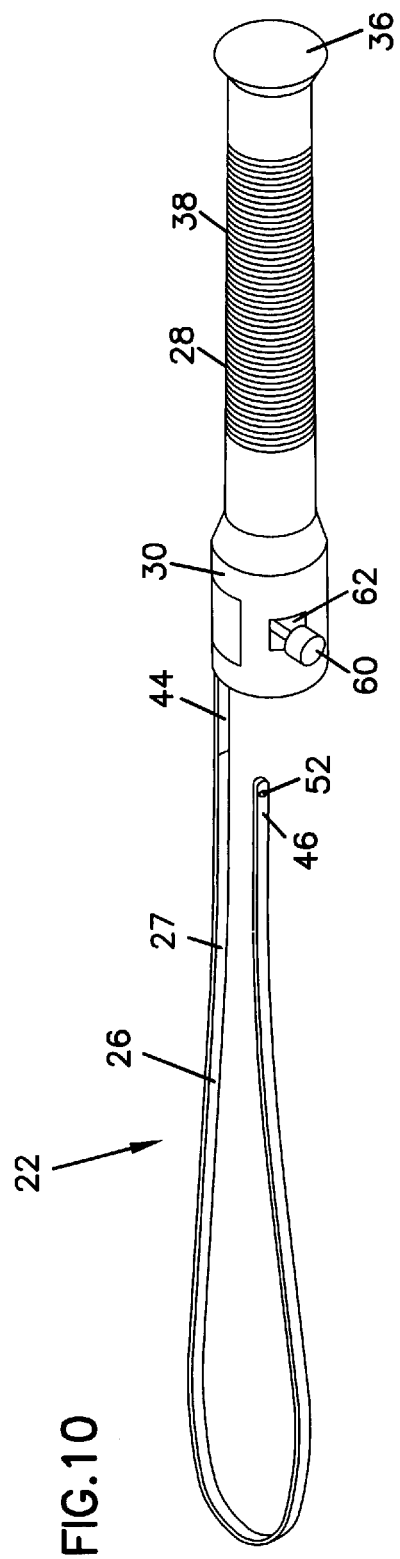
FIG. 10 is a perspective view of the delivery apparatus of FIG. 9 in an open position.

The releasing mechanism 42 operates to allow the user to release the second end 46 of the band 26 from the handle 24, thus converting the hoop structure into an open ended line (see FIG. 10). In one embodiment shown in FIGS. 10 and 11, the second end 46 of the band 26 defines an aperture 52 for receiving an attachment pin 54 for holding the second end 46 of the band 26 in the interior cavity 41 of the engagement portion 30 of the handle 24. In the closed position, the attachment pin 54 is positioned in the hole 52, retaining the band 26 in the handle. In the open position, the attachment pin 54 slides out of the hole 52 to release the band from the handle. Note that an aperture in the band end is a preferable manner for engaging the releasing mechanism. Hooks, pins, or other pieces that extend off of the band could damage the heart or jacket during use.

In more detail, the releasing mechanism 42 of this embodiment includes an attachment pin 54 positioned on a platform 56, a biasing spring 58, and a push button pin 60. The biasing spring 58 exerts an upward biasing force on the platform 56 and attachment pin 54. In this position the attachment pin 54 sits within the aperture 52 securing the second end 46 of the band 26 to the platform 56 in the interior portion 40 of the engagement portion 30 of the handle 24. The upward force also exerts a positioning force on the push button pin 60. To release the second end 46 of the band 26, the push button pin 60, which extends through an aperture 62 in the engagement portion of the handle, is pushed in a downward direction to counteract the upward force generated by the spring 58. The downward force causes the platform 56 and attachment pin 54 to slide downward, releasing the second end 46 of the band 26 from the handle 24.

The push button pin 60 is typically positioned to extend out of the engagement portion 30 of the handle 24. Preferably, the push button pin 60 is positioned so that a user can trigger release the band 26 using his or her thumb or index finger.

Figure 12:
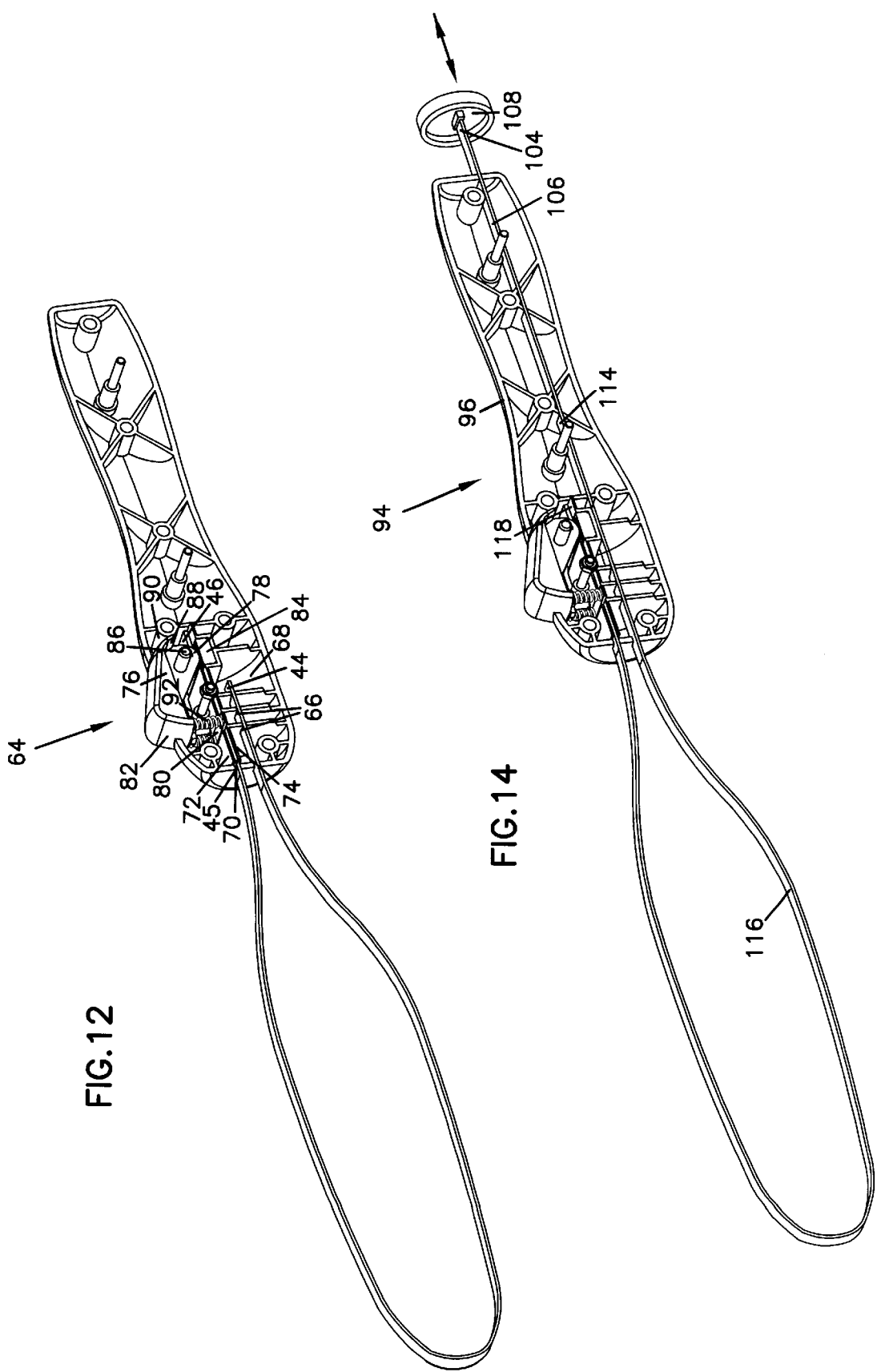
FIG. 12 is a representative cut away view illustrating an alternative embodiment of the releasing mechanism of the delivery apparatus.

An alternative releasing mechanism 64 embodiment is shown in FIG. 12. As in the previous embodiment, the first end 44 of the band is mounted to the engagement portion 30 of the handle, preferably at the interior 40 of the engagement portion 30. A series of retaining slots 66 may be positioned along the interior surface 68 of the handle to help align the first end 44 of the band 26 with the attachment site in the handle. Attachment to the interior surface 68, as above, is through any number of well known means, including, but not limited to, adhesives, brackets, bolts, rivets, screws, mating slots, insert molding, contained enlarged or bent end, pin through a hole, etc.

The releasing mechanism 64 shown in FIG. 12 operates to allow the user to release the second end 46 of the band 26 from the handle. A groove 70 is formed within the interior of the engagement portion of the handle for aligning and supporting the second end 46 of the band 26 inside the handle at the releasing mechanism 64. The groove 70 is formed from two substantially horizontal portions 72 and 74 that extend off of the interior cavity surface of the handle and that align with the slot 45 in the face 75 of the engagement portion of the handle. Preferably, the two horizontal portions 72 and 74 are formed as integral parts of the handle 26 and are not independent pieces attached to the interior cavity surface in the handle. Typically, the groove 70 is of a sufficient size and shape to allow band movement into and out of the handle and yet maintain proper positioning of the band in relation to the rest of the releasing mechanism. Other structures beyond a groove may be substituted for aligning and supporting the band within the handle, for example, retaining slots, indentations, brackets, etc.

Typically, the top portion 72 of the groove 70 is discontinuous having a break or opening within which a cam 76 having a spring biased cam surface 78 exerts a direct frictional force on the second end 46 of the band 26. Preferably, the top portion 72 of the groove 70 also defines a second opening within which sits a secondary brake pad 80 that extends downward from the front 82 of the cam 76. The bottom portion 74 of the groove 70 preferably defines a housing for an enhanced frictional surface 84 that aligns under the band and axially aligned with the cam surface 78. In this manner, the second end 46 of the band 26 is frictionally sandwiched between the cam surface 78 and the lower positioned frictional surface 84.

In the locked position, i.e., the releasable second end 46 of the band 26 is engaged by the handle, a cam 76 exerts a frictional force through the cam surface 78 onto the second end 46 of the band 26. The frictional force on the band is enhanced by the lower frictional surface 84. To release the second end 46 of the band 26 from the cam surface 78, the cam 76 is actuated around a swivel 86, which releases the cam surface 76 from the second end 46 of the band 26 and which frictionally secures a rear edge 88 of the cam 76 to an extension 90 on an interior surface 68 of the handle. In this position the cam surface 78 is held off the band. The force used to actuate the cam 76 around the swivel 86 conversely compresses a spring 92 downward on the secondary brake pad 80, which frictionally holds the band 26 in place until the user releases the downward force. In this position, the user controls the release of the band's second end 46 from the handle by relief of the downward pressure because the cam surface is no longer engaged to the band. Once the user releases pressure on the secondary brake pad, the secondary brake pad is released from the band, and the second end 46 of the band is free to be pulled out of the groove 70, and hence out of the handle.

To return the second end 46 of the band 26 to the handle, it is aligned within the groove 70, and the edge 88 is moved off of the handle so that the cam surface 78 is engaged with the band 26.

In an alternative embodiment, the releasing mechanism has a cam that contacts the band through the cam surface. In the locked position, the cam surface is spring biased on the band surface again sandwiching the band between the cam and the frictional surface. Swiveling the cam forward compresses the spring(s) on an anchored portion of the handle and releases the cam surface from the band, allowing the band to be released from the handle. Release of the compressing force on the spring(s) allows the cam surface to swivel back to its original spring biased position on the band. Thus, to lock the band in the handle, the band is aligned under the cam and the cam surface allowed to frictionally engage the band.

Figure 13:
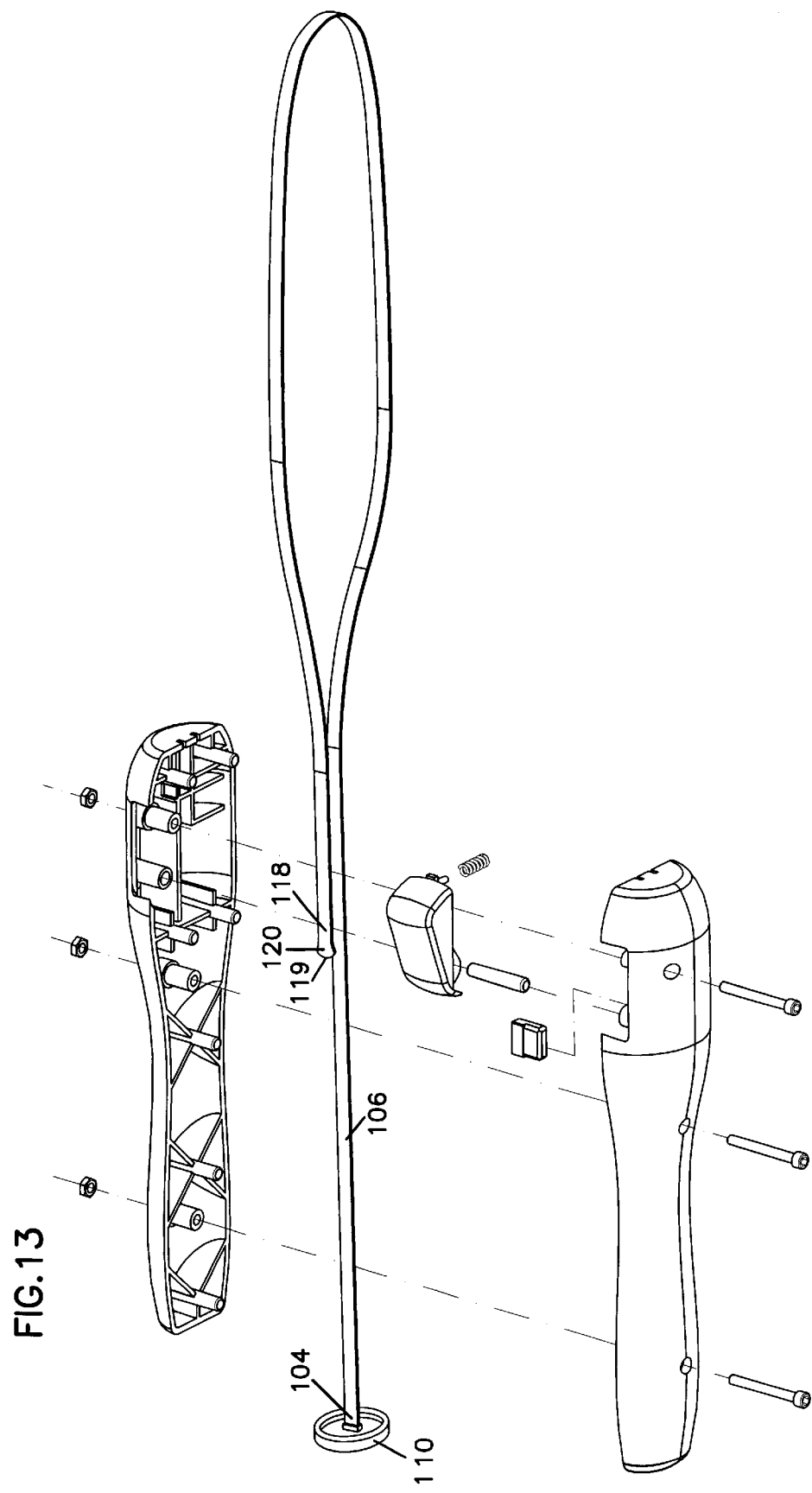
FIG. 13 is a representative exploded view illustrating an alternative embodiment of the delivery apparatus.

In yet another alternative embodiment of the releasing mechanism 94 (see FIGS. 13 and 14), the handle 96 has an interior cavity 98 defined in both the engagement 100 and grip portions 102. The first end 104 of the band 106 is mounted or fastened to an internal surface 108 of a releasable end cap 110 located at the distal end 112 of the grip portion 102. Preferably, the first end of the band is rotatably mounted or fastened to the internal surface of the releasable end cap. The releasable end cap 110 is fit to the handle through any of a number of well known means that include, but are not limited to, snap fitting, threaded engagement, leur lock, etc.

The contained band 114 is lengthened so that it runs through the full length of the handle to the releasable end cap 110. Guides, tracks, retaining slots or grooves may be located within the handle to slidably align and position the band within the handle and to the releasable end cap. Note that the exposed band 116 lengths are similar to those discussed above. The second end 118 of the band 106 is releasably engaged to the handle 96 as per any of the embodiments discussed above, for instance using a cam or releasing pin, etc.

To remove the band 106 from the cardiac constraint jacket 10, the second end 118 of the band 106 is released from the handle using a cam, releasing pin, etc. Once released from the handle 96 the second end 118 of the band may be threaded out of the receiving member 17 located around the cardiac constraint jacket. However, unlike the embodiments discussed above, the band 106 is not threaded through the receiving member 17 by pulling the handle away from the jacket 10. Rather, the releasable end cap 110 is released from the handle and pulled away from the handle, thus pulling the band 106 directly into and through the interior cavity 98 of the handle 96. In this manner the band 106 is withdrawn from the receiving member 17 in a clean and smooth motion out through the back of the handle. The movement of the second end 118 of the band 106 directly into the handle 96 prevents recoil of the band 106 when the free or second end 118 of the band 106 exits the receiving member or other band engaging material. The movement also improves the user control over the removal of the band from the cardiac constraint jacket.

It is also noted that the second end 118 of the band 106 may be widened slightly at or around the tip 119. The upper groove in the handle is widened to accept the widened band end 120, and does not interfere with the releasing mechanisms discussed previously. However, the first end slot in the engagement portion face, or the retaining slots within the internal chamber of the handle, are formed not to accept the widened second end 120, thus preventing the widened end 120 from being pulled into or completely through and from the handle.

It can be recognized by those skilled in the art that other releasing mechanisms can operate to release one end of the band from the handle. The discussion above simply provides illustrations of possible releasing structures, other structures, well known to the art, are envisioned to be within the scope of the present invention. This includes releasing mechanisms as simple as manually sliding the aperture in the end of the band onto and off of a retaining pin or hook on the handle, or sliding the end of the band into a retaining groove in the handle. In these cases the user would simply manually move and release the band end off of the handle.

It is also envisioned that embodiments of the present invention have a releasing mechanism that is not part of the handle. Here, a hook or pin on the band itself could releasably engage the aperture in the second end of the band. The hook is positioned close to the handle, toward the first end of the band, so as to not interfere with the positioning of the jacket or come in contact with the heart. To release the band the user simply slips the second end of the band off of the hook toward the first end of the band.

An embodiment of the present invention may also include a band that can be released at both of its ends. For example, an apparatus that has a first releasing trigger to release the first end of the band and a second releasing trigger to release the second end of the band, or one trigger that releases the handle from a band having a pre-set hoop structure.

In yet another embodiment of the present invention, a first end of the band is fixedly attached to the handle, while the second end is free of the handle. The shape memory properties of the band material shape the band substantially to a hoop like structure, with the second end being free and adjacent the handle. This embodiment preferably works with band material that has good lateral strength and shape memory properties.

In another embodiment of the present invention, the hoop like structure of the apparatus is composed of two fairly equal length band portions, where both band portions have one end fixedly attached to the handle. The two band portions can form a hoop like structure with a break in the middle, or can have a releasable engagement mechanism to connect the two independent band portions together. Engagement means between the two band portions are well known in the art. In either case, the jacket is loaded and removed from the band at the middle break of the band. Here during use of the apparatus there is no gap between the two portions of the band. In all other manners the embodiment is similar with embodiments already discussed in this disclosure.

Embodiments of the present invention can also be used to place the jacket 10 on a heart H where the parietal pericardium is intact. In order to position the jacket 10 over the apex A of the heart H, the jacket is opened along a line extending from the upper end 12' to the lower end 14' of the jacket 10'. Like the embodiment directly above, in this embodiment of the delivery apparatus, the band 26 is composed of two independent band portions. However, in this embodiment, a gap or break if formed between the two portions (as such, one portion is likely shorter in length than the other portion). The opening along the jacket 10 from the upper end 12' to the lower end 14' is aligned with the gap formed between the band pieces, so that the opened jacket and opened band can be moved up and past the pericardial surface of the heart H. The opposing edges of the opened jacket are secured together. In this embodiment, both ends of the band can be either fixedly fastened to the handle or releasably mounted to the handle.

Referring to FIG. 15 for delivery of the jacket to the heart, a delivery apparatus having a hoop like band is deformed to provide an opening 122 for fitting around the heart H. When nitinol, or other material having memory-activated properties, is utilized, a preferred shape for the band can be induced and maintained. The band is manipulated to deform into a shape for fitting over the heart H. Ad discussed above, the band is fairly flexible and able to be manipulated into any shape. The band maintains the inputted shape until a sufficient compression or decompression force is exerted on the band to alter the existing shape. Additionally, the band has lateral strength as not to bend in the axial direction under normal use conditions. Example nitinol configurations include: 0.040 inches×0.140 inches nitinol strength, and straight line versus curved line dimensions include, but are not limited to, ≧0.025 inches×0.140 inches, 0.030 inches× 0.140 inches, or 0.035 inches×0.0140 inches; note that nitinol sizes are dependent on band length.

Figure 16:
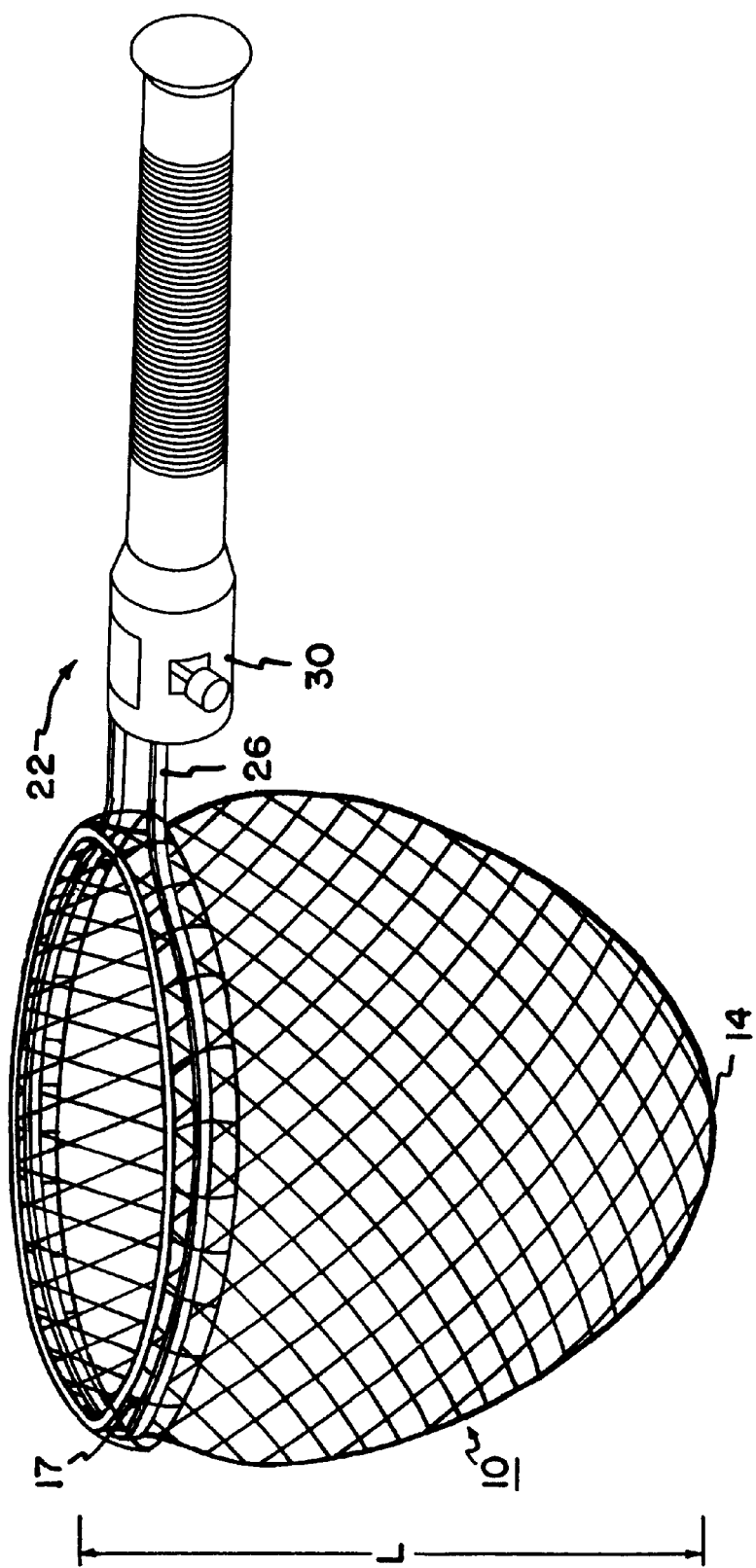
FIG. 16 is a side view of the delivery apparatus engaged to a cardiac constraint jacket.

A cardiac constraint jacket 10 loaded on the delivery apparatus is shown in FIG. 16. The band 26 is received in the receiving member 17. As previously discussed, the receiving member 17 can be continuous around the jacket 10 or be discontinuous, as long as it receives the band and allows the open upper end of the jacket to substantially take on the shape of the band 26.

Figure 17:
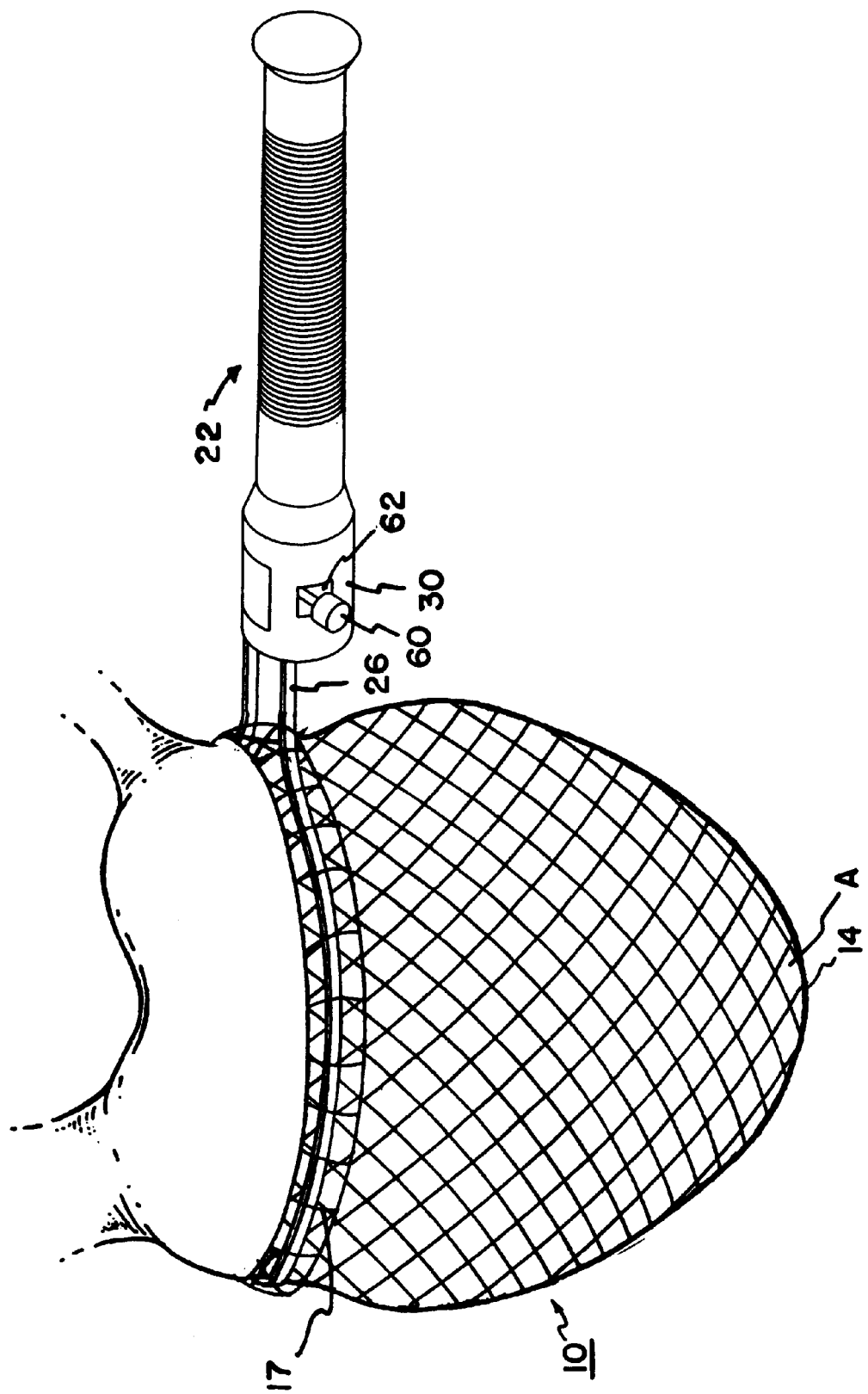
FIG. 17 is a side view illustrating the delivery apparatus delivering a cardiac constraint jacket onto a diseased heart.

In one embodiment of the present invention, the jacket 10 is loaded on the delivery apparatus when the tapered second end 46 of the band 26 is released from the handle 24 and put through an opening in the receiving member 17. The receiving member 17 is threaded over and along the band 26 toward the first end 44 of the band 26. The jacket 10 is uniformly positioned on the band 26 and preferably centered between the first and second ends, 44 and 46 respectively. Once the receiving member 17 is fully loaded on the band 26, the second end 46 of the band 26 is re-attached to the engagement portion of the handle. The band can then be deformed to the desired shape for fitting the jacket onto the heart H. Note that the band can also be deformed to the desired shape prior to the jacket being received and threaded onto the band. As the band 26 is moved over the heart H it positions the jacket 10 so that the jacket 10 can be properly positioned on the heart H (see FIG. 17). Once the jacket 10 is positioned on the heart H, the second end 46 of the band 26 is released, and the band 26 pulled along and out of the receiving member 17. The positioned jacket can then be snugly fit to the heart H during diastole as fully discussed above.

Figure 18:
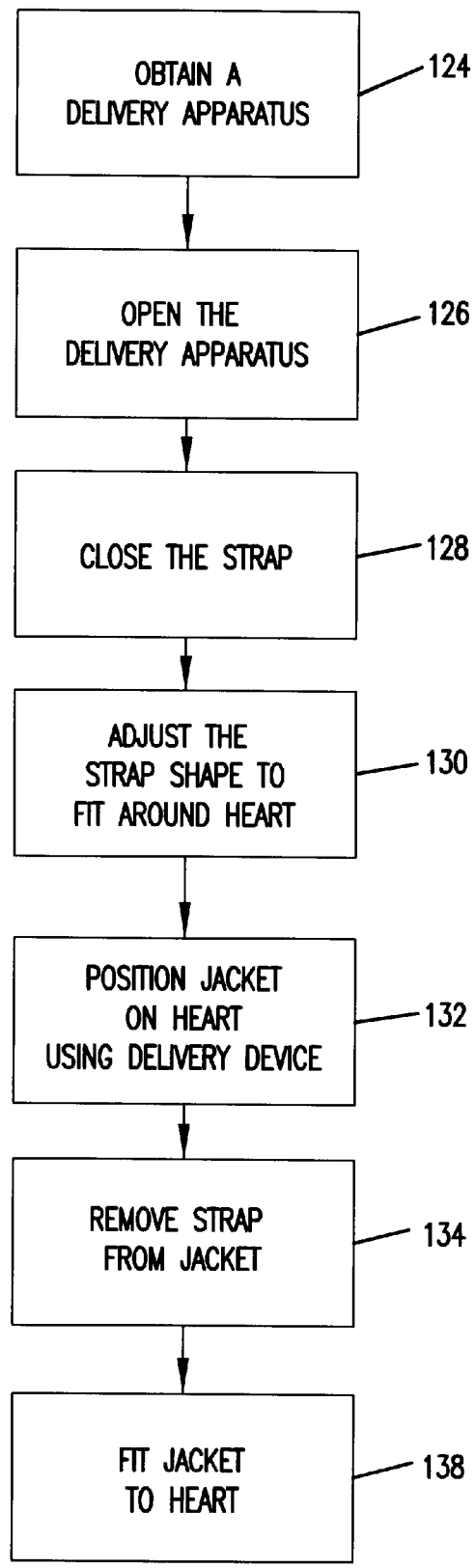
FIG. 18 is a flow diagram of the method of fitting a jacket on the heart using a delivery device in accordance with an embodiment of the invention.

One method for positioning the cardiac constraint jacket on the heart is shown in FIG. 18. In step 124, a delivery apparatus and jacket are obtained. In step 126, one end of the delivery apparatus is released, providing a free end of the band. In step 128, the released end of the band is traversed through the jacket receiving member to secure the jacket to the delivery apparatus. In step 130, the band is closed back on the handle. In step 132, the band, having the attached jacket, is deformed to fit around the heart H. In step 134, the band is moved over the heart so as to position the jacket on the heart H. In step 136, one end of the delivery device is released to open the band and the opened band is removed from the positioned jacket. Finally, in step 138, the jacket is fit and secured to the heart. It is noted that step 108, deforming the band, can occur before the band receives the jacket, i.e., step 104.

It will be clear that the present invention is well adapted to attain the ends and advantages mentioned as well as those inherent herein. While presently preferred embodiments have been described for purposes of this disclosure, various changes and modifications may be made which are well within the scope of the present invention. Numerous other changes may be made which will readily suggest themselves to those skilled in the art and which are encompassed in the spirit of the invention disclosed and as defined in the appended claims.

What is claimed is:

1. A delivery apparatus for positioning a cardiac constraint jacket on a heart, the delivery apparatus comprising:
   a handle;
   a band having a first end fastened to the handle and a second end releasably fastened to the handle;
   a releasing mechanism wherein the releasing mechanism fastens the second end of the band to the handle; and
   wherein a portion of the cardiac constraint jacket is configured to be attached on the band via the second end of the band for subsequent delivery and positioning of the cardiac constraint jacket on the heart.

2. A delivery apparatus for positioning a cardiac constraint jacket on a heart, the delivery apparatus comprising:
   a handle;
   a band having a first end fastened to the handle and a second end releasably fastened to the handle, wherein the second end of the band is tapered; and
   wherein a portion of the cardiac constraint jacket is configured to be attached on the band via the second end of the band for subsequent delivery and positioning of the cardiac constraint jacket on the heart.

3. The delivery apparatus of claim 1 wherein the band material is selected from the group consisting essentially of nickel-titanium alloy, titanium alloy, stainless steel, aluminum and composite materials.

4. The delivery apparatus of claim 1 wherein the band material is nickel-titanium.

5. The delivery apparatus of claim 1 wherein the band has a first malleable state for a substantial length of the band and a second malleable state for the remainder of the band, wherein the two malleable states differ.

6. The delivery apparatus of claim 5 wherein the second malleable state is greater than the first malleable state and wherein, the second malleable state is located at the second end of the band.

7. The delivery apparatus of claim 1 wherein the band material is a shape memory alloy.

8. The delivery apparatus of claim 1 wherein the band is annealed.

9. The delivery apparatus of claim 1 wherein the band maintains a hoop shape for fitting the band around the circumference of the heart.

10. The delivery apparatus of claim 1 wherein the releasing mechanism is triggered via a push button pin.

11. The delivery apparatus of claim 1 wherein the second end of the band has a hole for operable engagement to the push button pin.

12. The delivery apparatus of claim 1 wherein the releasing mechanism is a retaining groove in the handle for receiving the second end of the band.

13. The delivery apparatus of claim 1 wherein the releasing mechanism is triggered via a cam.

14. A device for treating cardiac disease of a heart, the heart having a longitudinal axis from an apex to a base and having an upper and lower portion divided by an A-V groove, the heart including a valvular annulus adjacent the A-V groove and ventricular lower extremities adjacent the apex, the device comprising:
   A. a cardiac constraint jacket, the cardiac constraint jacket comprising:
      i. a volume between an open upper end and a lower end, the cardiac constraint jacket dimensioned for the apex of the heart to be inserted into the volume through the open upper end and for the jacket to be slipped over the heart, the cardiac constraint jacket further dimensioned to have a longitudinal dimension between the upper and lower ends sufficient for the cardiac constraint jacket to constrain at least the lower portion of the heart;
      ii. a receiving member around the upper end of the jacket;
      iii. the cardiac constraint jacket adapted to be secured to the heart;
   B. A delivery apparatus for placing the cardiac constraint jacket on the heart, the delivery apparatus comprising:
      i. a handle;
      ii. a band having a first end fastened to the handle and a second end releasably fastened to the handle; and
      iii. releasing mechanism wherein the releasing mechanism fastens the second end of the band to the handle, wherein the receiving member of the cardiac constraint jacket is ibreaded on the band via the second end of the band for subsequent securing of the cardiac constraint jacket on the heart.

15. The delivery apparatus of claim 2 wherein the band material is selected from the group consisting essentially of nickel-titanium alloy, titanium alloy, stainless steel, aluminum and composite materials.

16. The delivery apparatus of claim 2 wherein the band material is nickel-titanium.

17. The delivery apparatus of claim 2 wherein the band has a first malleable state for a substantial length of the band and a second malleable state for the remainder of the band, wherein the two malleable states differ.

18. The delivery apparatus of claim 17 wherein the second malleable state is greater than the first malleable state and wherein, the second malleable state is located at the second end of the band.

19. The delivery apparatus of claim 2 wherein the band material is a shape memory alloy.

20. The delivery apparatus of claim 2 wherein the band is annealed.

21. The delivery apparatus of claim 2 wherein the band maintains a hoop shape for fitting the band around the circumference of the heart.

* * * * *